(12) United States Patent
Chen et al.

(10) Patent No.: US 12,138,153 B2
(45) Date of Patent: Nov. 12, 2024

(54) HEART VALVE SEALING ASSEMBLIES

(71) Applicant: Edwards Lifesciences Corporation, Irvine, CA (US)

(72) Inventors: Harvey H. Chen, Irvine, CA (US); Son V. Nguyen, Irvine, CA (US); Devin D. Nguyen, Westminster, CA (US); Diana Marie Edwards, Boulder, CO (US); August R. Yambao, Temecula, CA (US); Jyoti B. Rao, Brea, CA (US); Alyssa E. Kornswiet, Orange, CA (US); Lisong Ai, New York, NY (US); Stephen W. Tang, Placentia, CA (US); Edward Romero, Anaheim, CA (US); Kevin K. Dang, Garden Grove, CA (US); Meena Francis, Fullerton, CA (US); Louis A. Campbell, Santa Ana, CA (US); Grace Myong Kim, Seal Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 554 days.

(21) Appl. No.: 17/389,771

(22) Filed: Jul. 30, 2021

(65) Prior Publication Data
US 2021/0353408 A1 Nov. 18, 2021

Related U.S. Application Data

(63) Continuation of application No. PCT/US2020/015671, filed on Jan. 29, 2020.

(60) Provisional application No. 62/798,901, filed on Jan. 30, 2019.

(51) Int. Cl.
*A61F 2/24* (2006.01)

(52) U.S. Cl.
CPC .......... *A61F 2/2409* (2013.01); *A61F 2/2412* (2013.01); *A61F 2/2418* (2013.01); *A61F 2220/0075* (2013.01); *A61F 2250/0048* (2013.01); *A61F 2250/006* (2013.01)

(58) Field of Classification Search
CPC .... A61F 2/2409; A61F 2/2412; A61F 2/2418; A61F 2220/0075; A61F 2250/0048; A61F 2250/006
See application file for complete search history.

(56) References Cited

U.S. PATENT DOCUMENTS

2006/0195185 A1* 8/2006 Lane ................... A61F 2/2412
623/2.38

* cited by examiner

*Primary Examiner* — Suba Ganesan
(74) *Attorney, Agent, or Firm* — Guy Cumberbatch

(57) ABSTRACT

A hybrid heart valve prosthesis that can be quickly and easily implanted during a surgical procedure is provided. The hybrid heart valve includes a substantially non-expandable, non-compressible prosthetic valve member having a peripheral sealing ring and an expandable stent frame projecting from an inflow end, thereby enabling attachment to the annulus without sutures. The stent frame may be plastically-expandable and may have a thin fabric layer covering its entirety as well as secondary sealing structures around its periphery to prevent paravalvular leaking. Other sealing solutions include interactive steps at the time of valve implant to establish seals around the stent and especially between the stent and the sealing ring of the valve member.

11 Claims, 19 Drawing Sheets

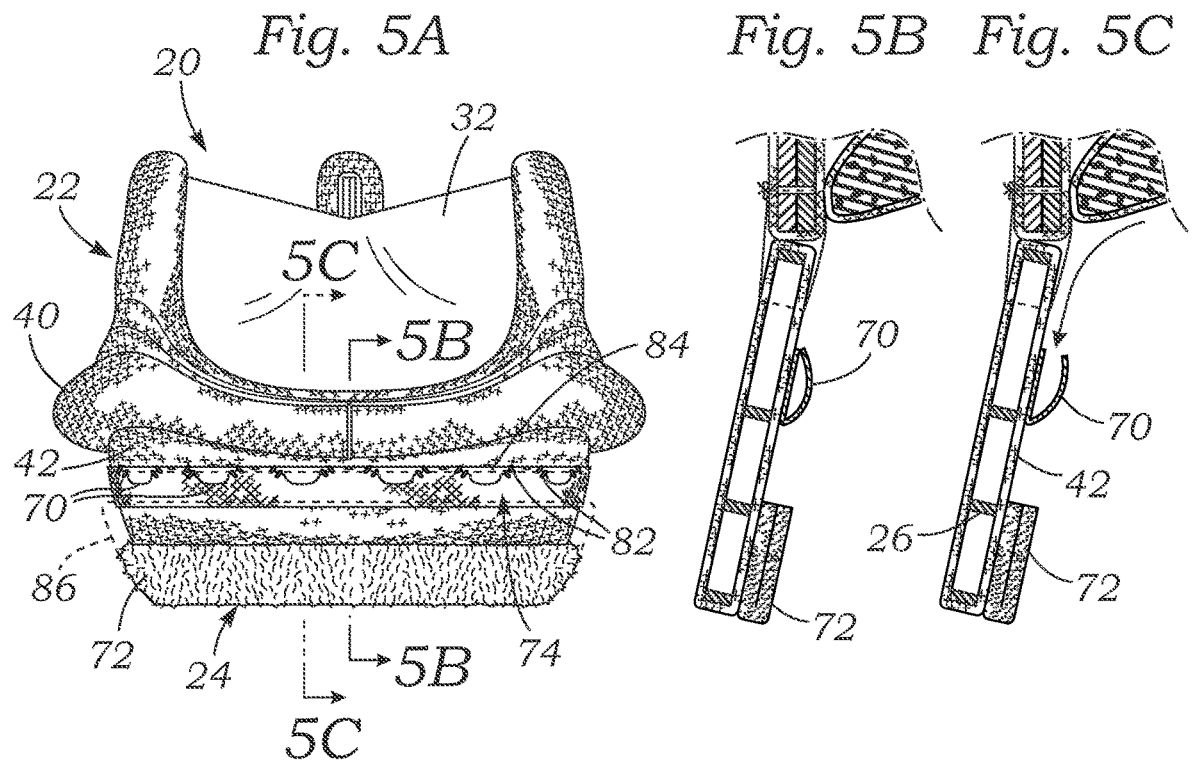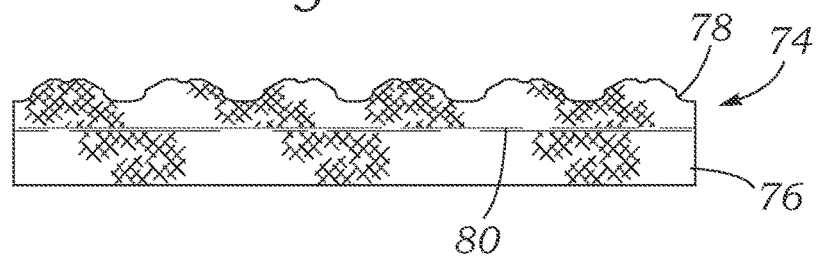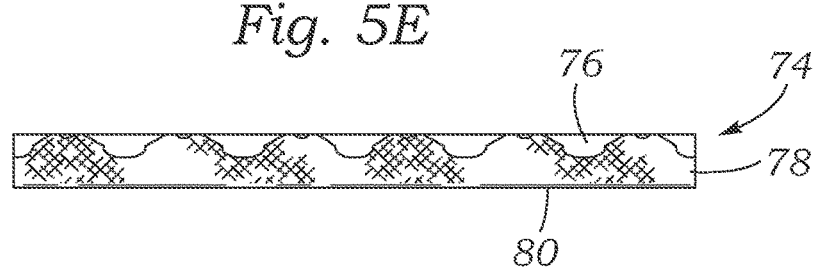

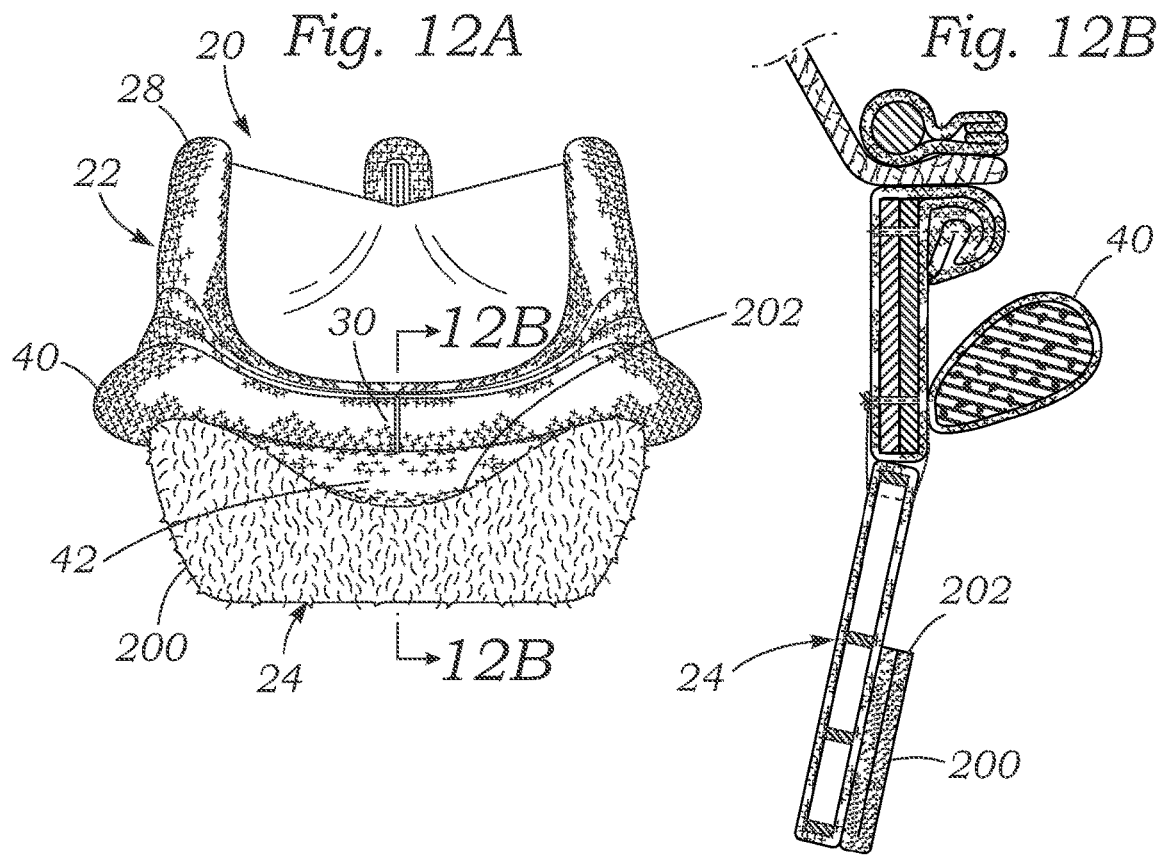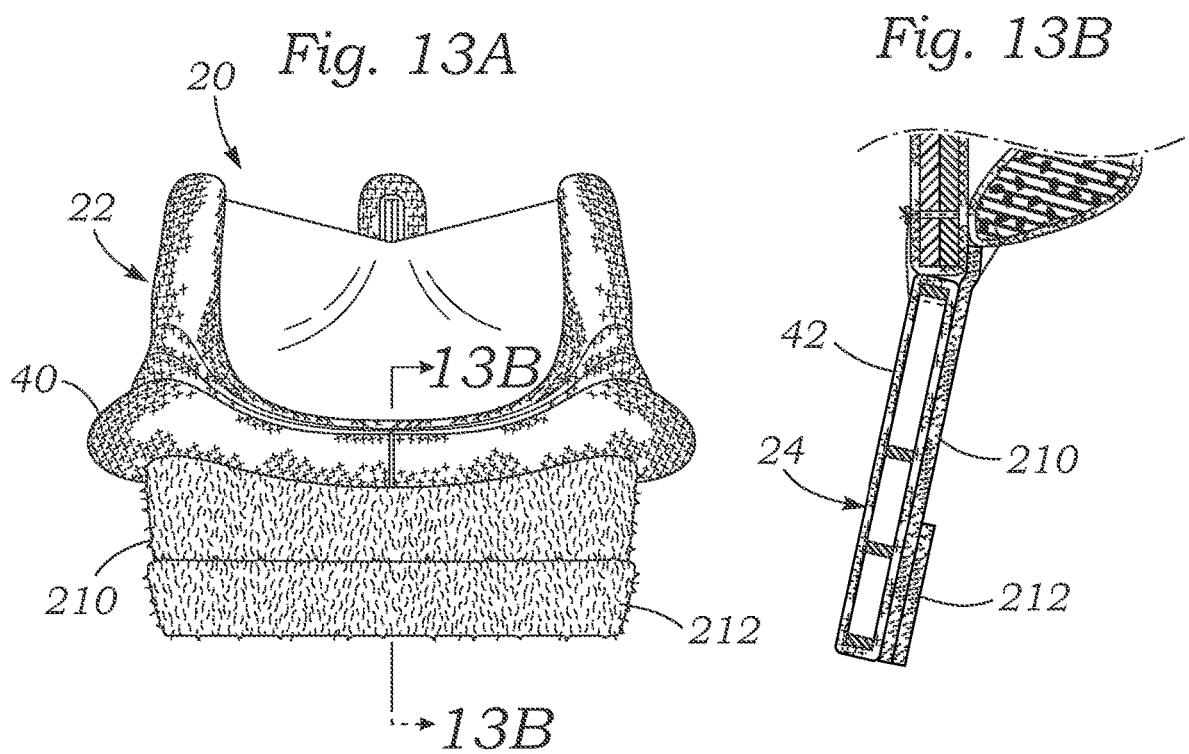

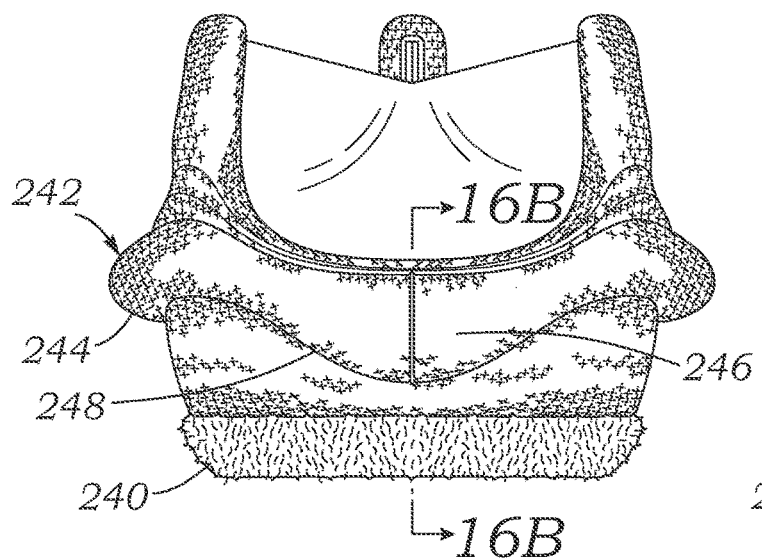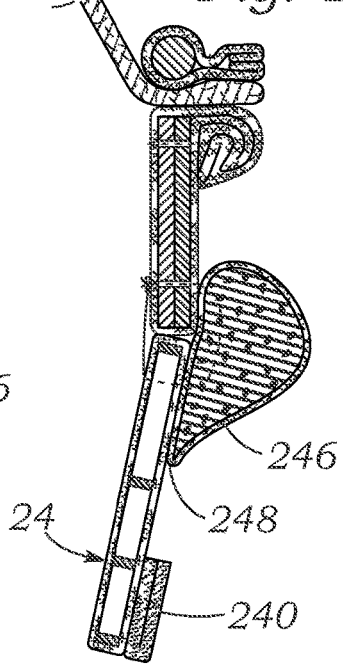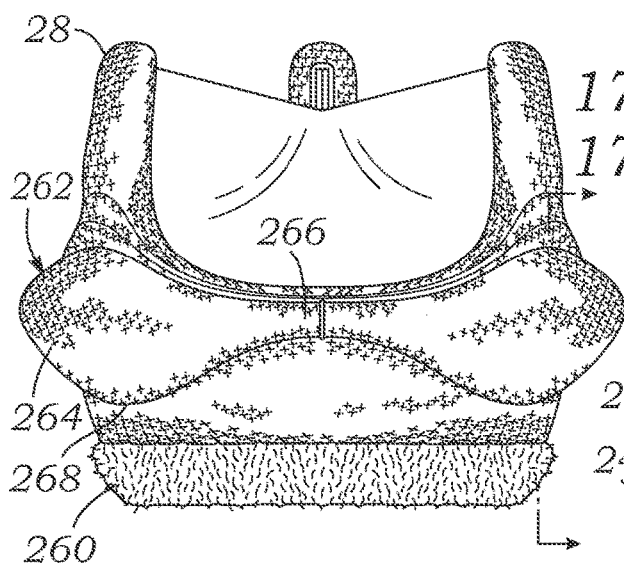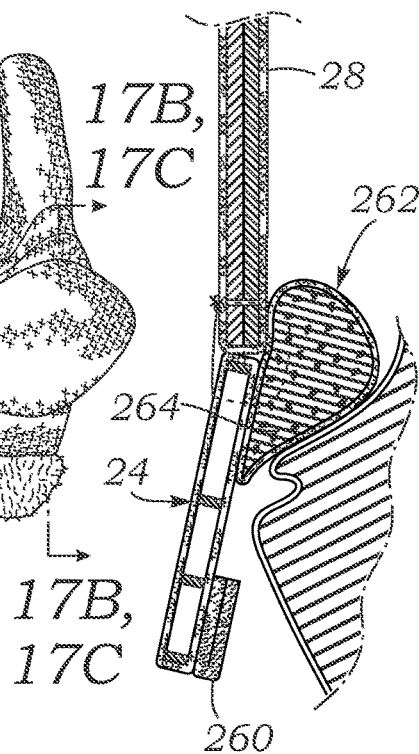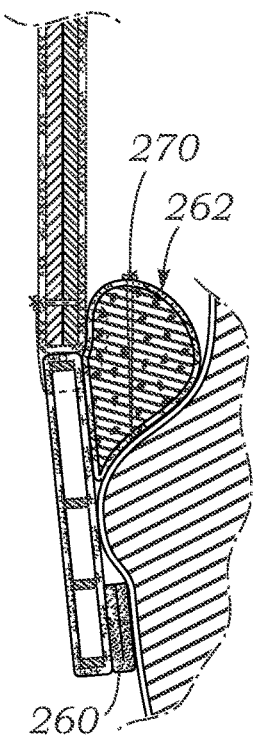

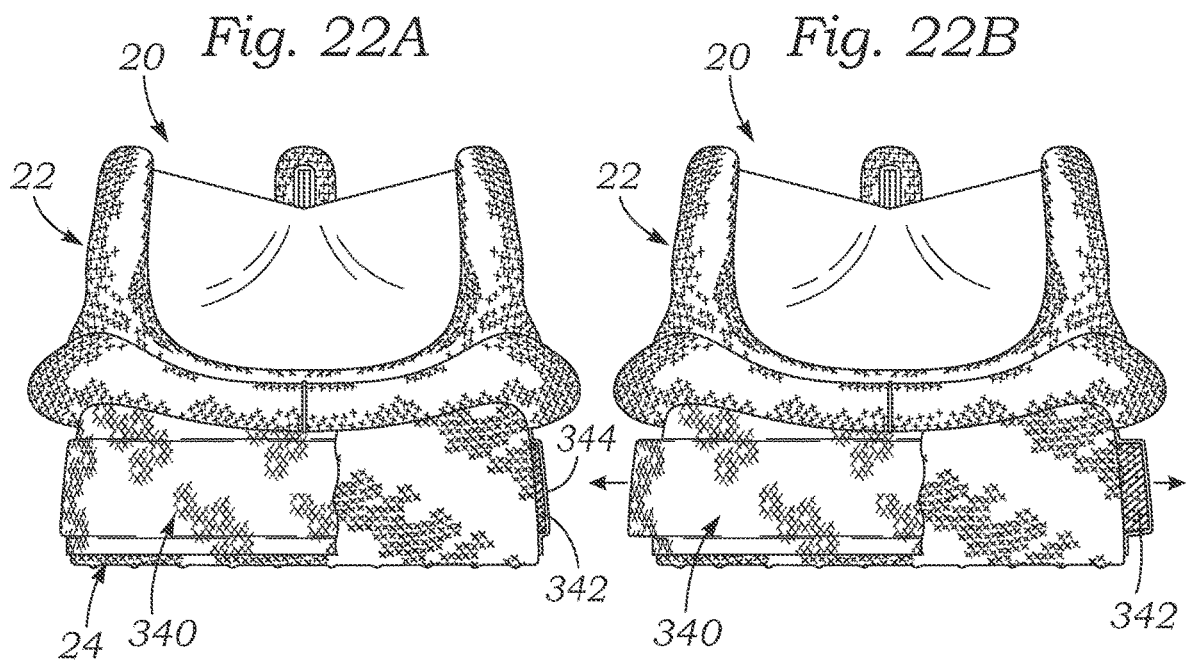
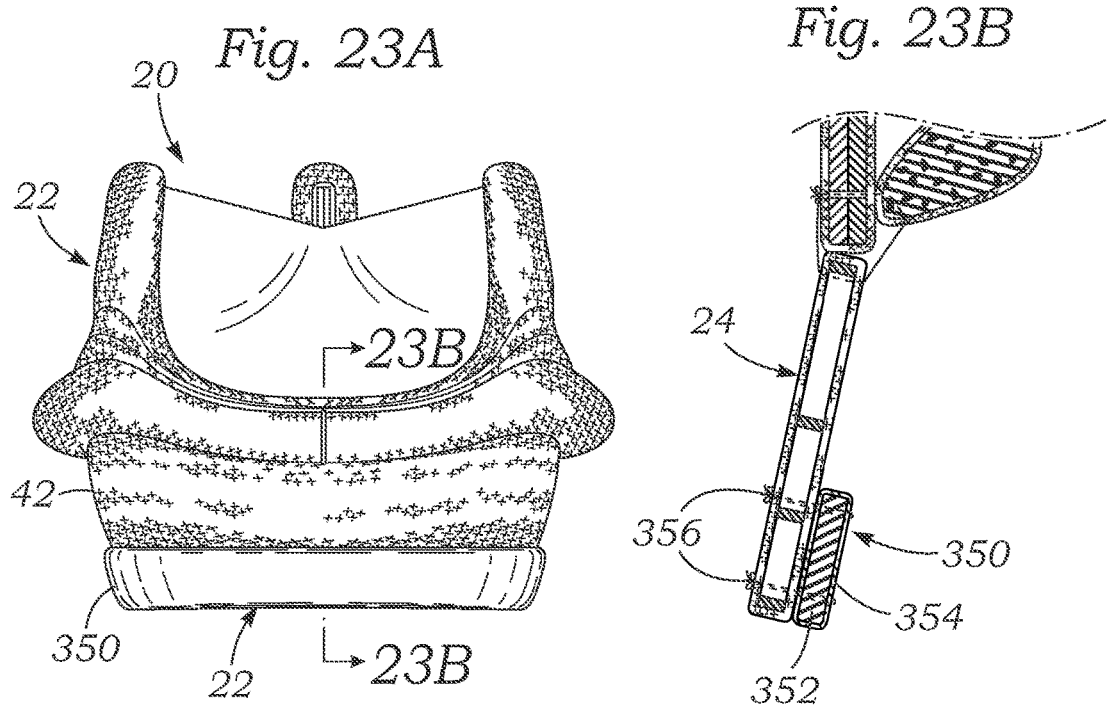

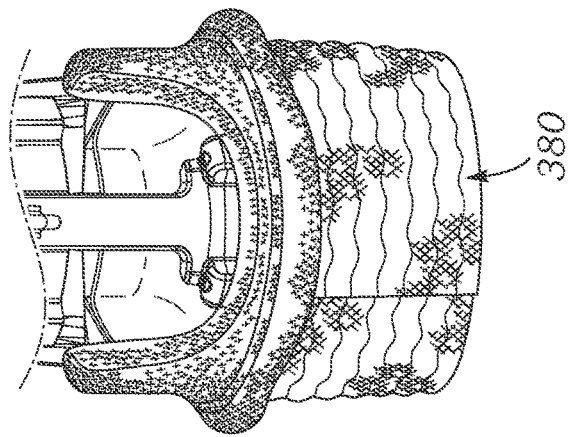
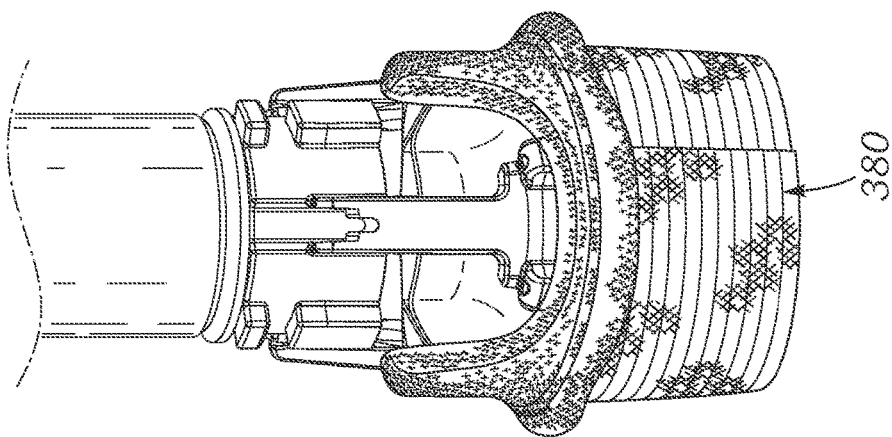
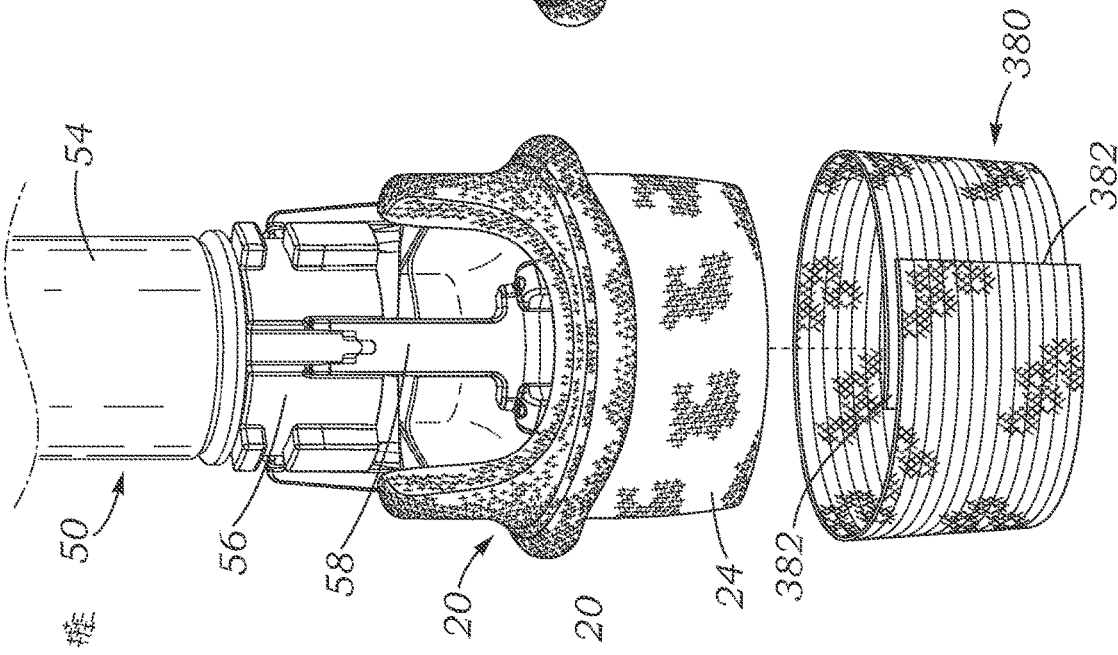

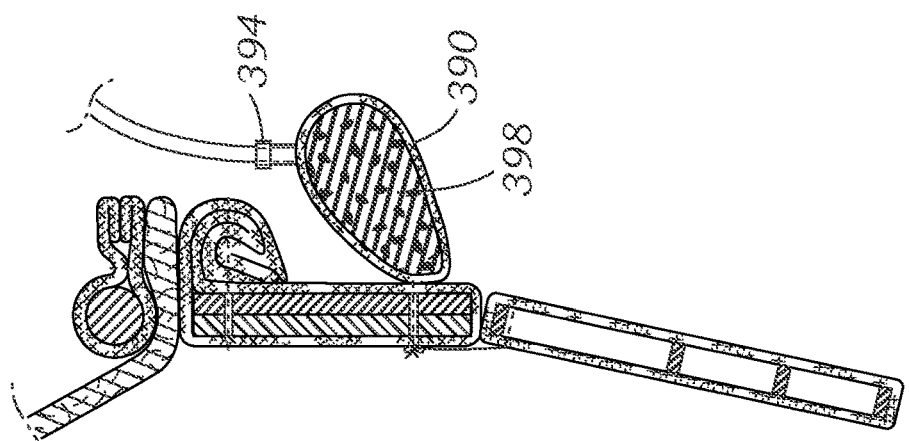
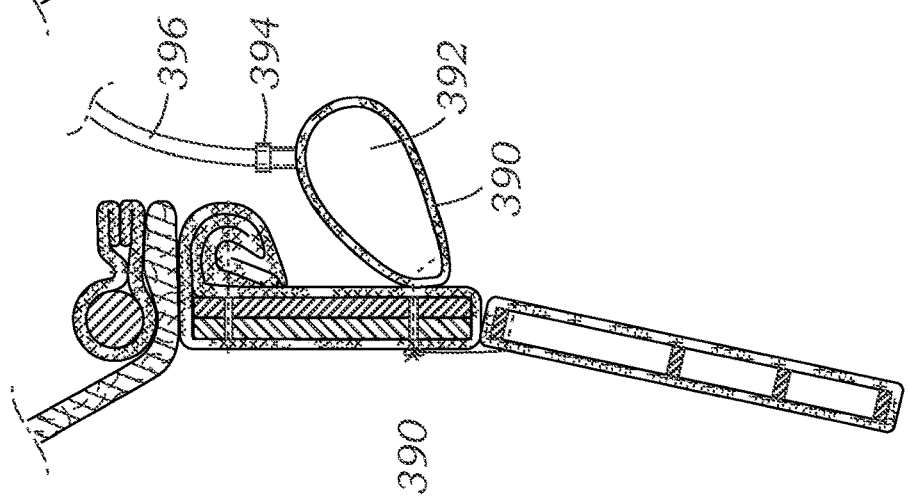
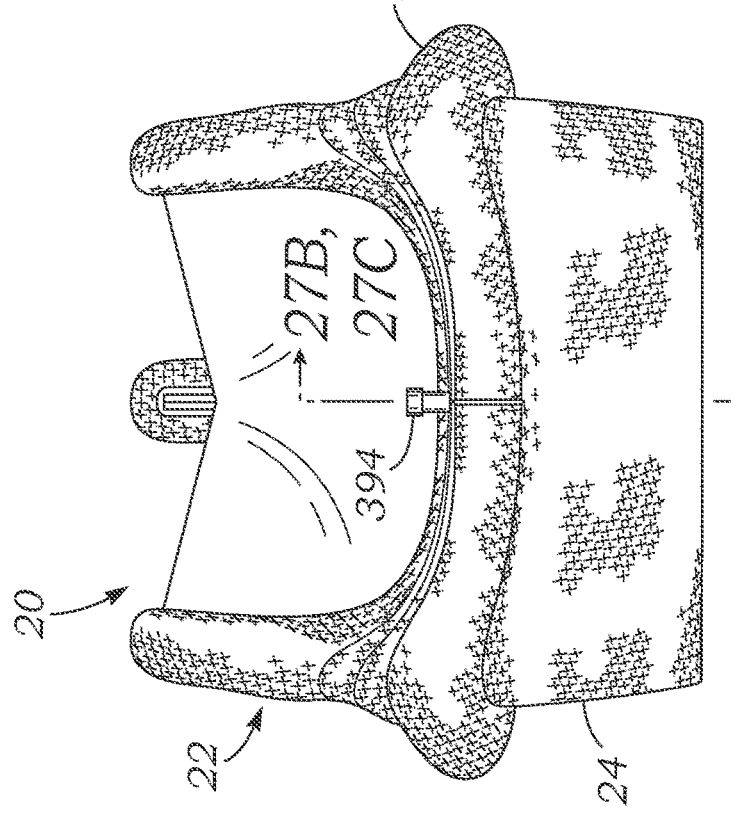

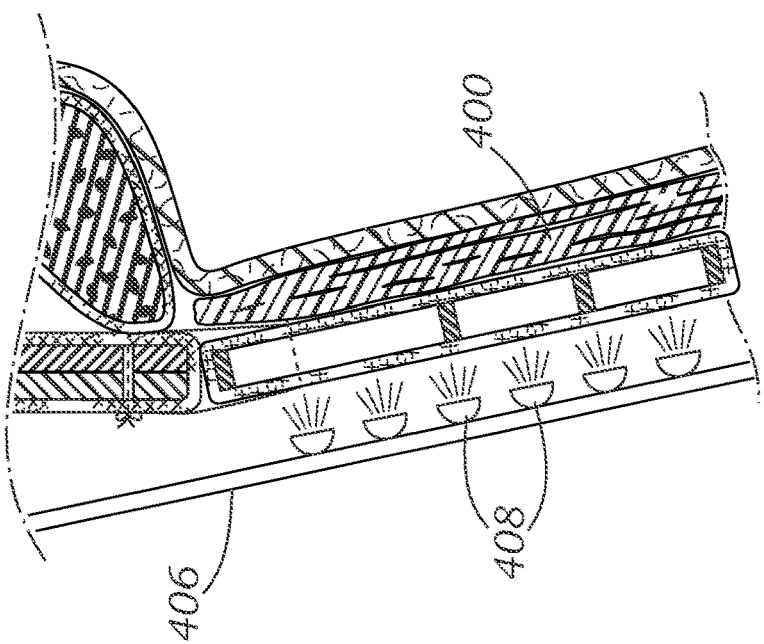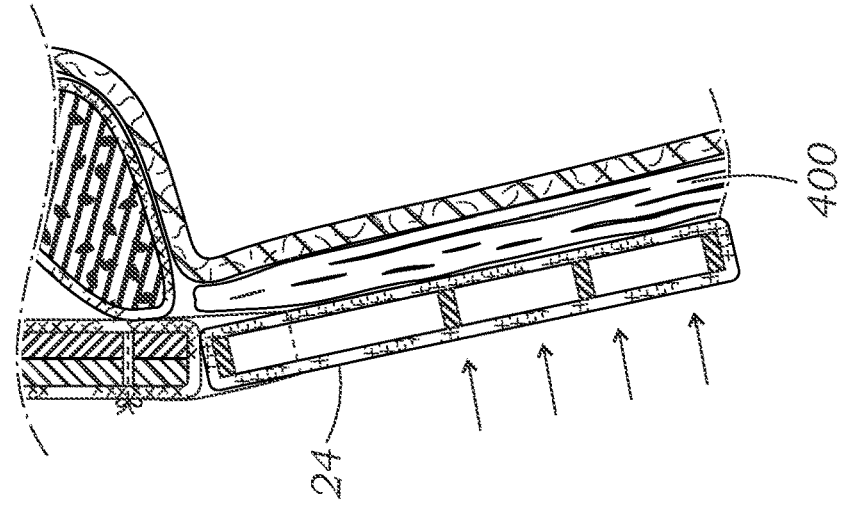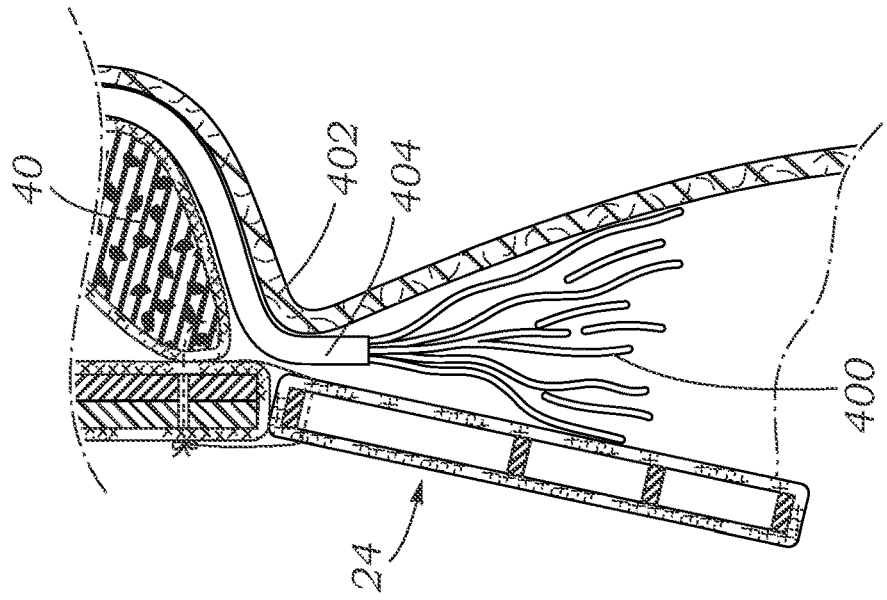

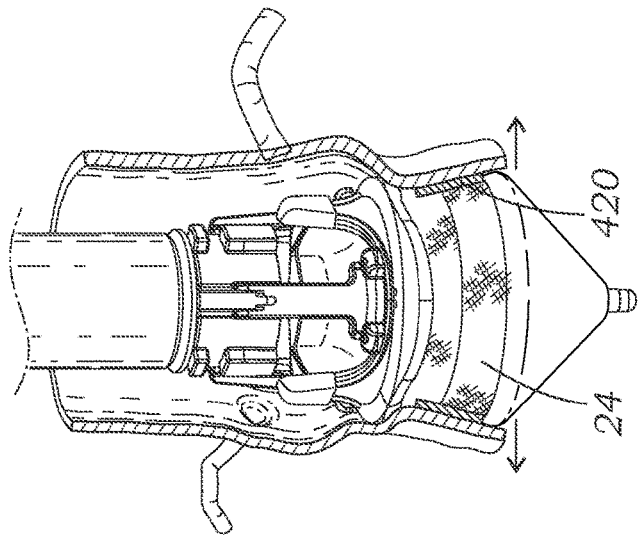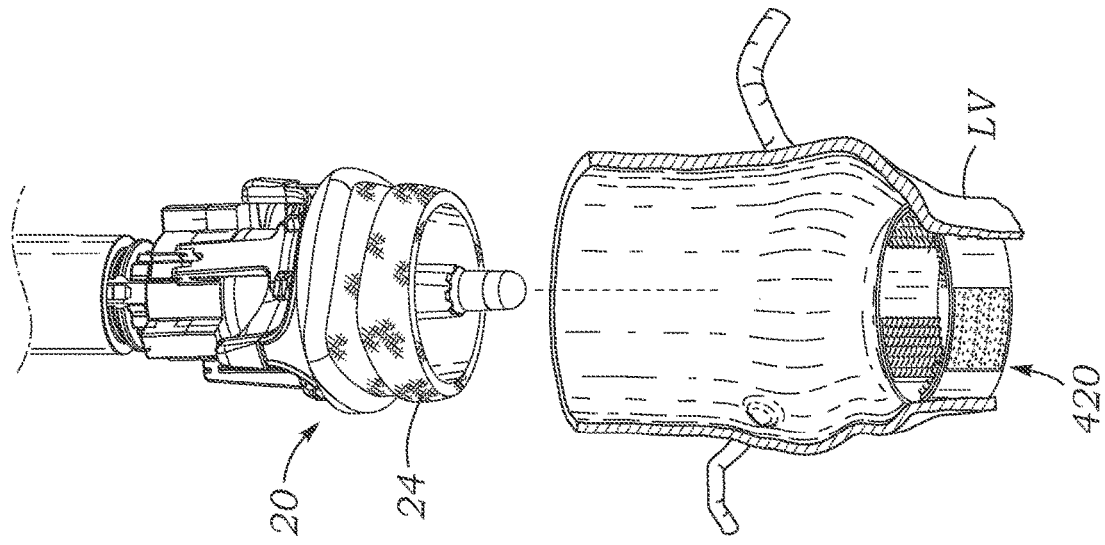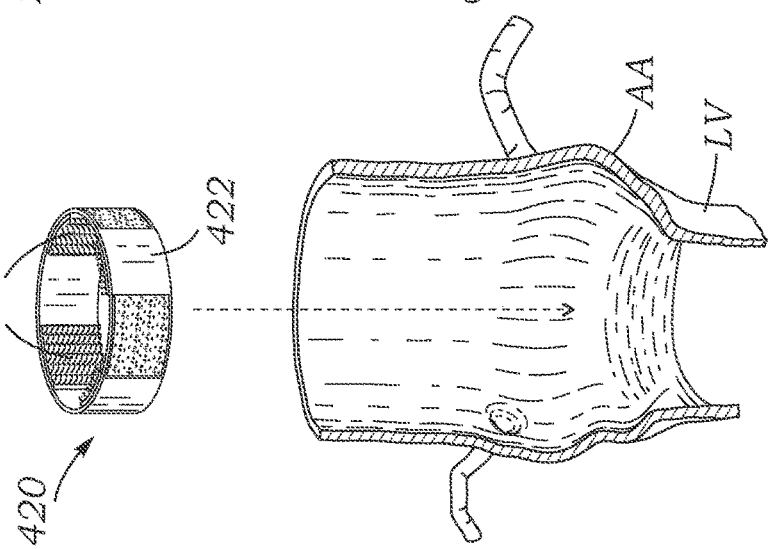

HEART VALVE SEALING ASSEMBLIES

CROSS REFERENCE TO RELATED APPLICATION

This application is a continuation of PCT Application PCT/US20/15671, filed Jan. 29, 2020, which claims the benefit of U.S. Patent Application No. 62/798,901, filed Jan. 30, 2019, the entire disclosures all of which are incorporated by reference for all purposes.

TECHNICAL FIELD

The present disclosure generally relates to prosthetic valves for implantation in body channels. More particularly, the present disclose relates to sealing solutions for hybrid surgical prosthetic heart valves configured to be surgically implanted in less time than current valves.

BACKGROUND

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. The problem with surgical therapy is the significant insult it imposes on these chronically ill patients and consequent high morbidity and mortality rates.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a non-expandable prosthetic surgical valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure.

Because of the drawbacks associated with conventional open-heart surgery, percutaneous and minimally-invasive surgical approaches are garnering intense attention. In one technique, and expandable prosthetic valve is configured to be implanted in a much less invasive procedure by way of catheterization. Although these remote implantation techniques have shown great promise for treating certain patients, replacing a valve via surgical intervention is still the preferred treatment procedure.

Accordingly, there is a need for a prosthetic valve that can be surgically implanted in a body channel in a more efficient procedure so as to reduce the time required on extracorporeal circulation. One solution especially for aortic valve replacement is provided by the Edwards Intuity valve system available from Edwards Lifesciences of Irvine, CA Aspects of the Edwards Intuity valve system are disclosed in U.S. Pat. No. 8,641,757 to Pintor, et al. The Edwards Intuity valve is a hybrid of a generally non-expandable valve member and an expandable anchoring stent that helps secure the valve in place in a shorter amount of time. The implant process only requires three sutures which reduces the time-consuming process of tying knots. A delivery system advances the Edwards Intuity valve with the stent at the leading end until it is located within the left ventricle, at which point a balloon inflates to expand the stent against the ventricular wall. The long handle and delivery system design facilitate access through smaller incisions (mini-sternotomy or right anterior thoracotomy) to avoid conventional full sternotomies.

Despite significant progress in improving the outcomes of surgical heart valve replacements, blood leakage around implanted valves remains a primary concern.

SUMMARY

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (e.g., cardiopulmonary bypass pump).

Various embodiments of hybrid prosthetic heart valve for implant at a heart valve annulus are disclosed herein. The heart valves each comprise a valve member having a non-expandable, non-collapsible annular support structure defining a flow orifice and having an inflow end, the valve member having valve leaflets attached to the support structure and mounted to alternately open and close across the flow orifice and a compressible sealing ring encircling the inflow end of the annular support structure. An expandable stent secured to the inflow end of the annular support structure extends therefrom to an inflow edge, the stent comprising a generally tubular stent frame formed by struts, the stent frame being covered both inside and out by a thin fabric.

Each hybrid prosthetic heart valve also includes supplemental sealing solution or structure on the expandable stent for sealing against paravalvular leakage past the valve.

One such sealing solution includes a narrow band of fabric circumscribing the stent outside of the thin fabric forming a series of pockets around the stent open to an inflow direction. The heart valve may further include a plush fabric cuff surrounding the thin fabric around the inflow edge of the expandable stent, wherein the band of fabric is located approximately midway along the expandable stent, spaced from both the plush fabric cuff and the inflow end of the annular support structure. Alternatively, the band of fabric extends between the plush fabric cuff and the compressible sealing ring and is attached at interrupted locations to the compressible sealing ring to form pockets between the interrupted locations. Still further, the band of fabric is located immediately above the plush fabric cuff, or the band of fabric is secured around the plush fabric cuff, or the plush fabric cuff may instead be secured on top of the band of fabric. In a preferred form, the band of fabric comprises a folded-over sheet of fabric with a rear portion separated from a crenellated front portion at a longitudinal fold line, and the pockets are formed in valleys between peaks of the crenellated front portion.

A second sealing structure is a flap of fabric having a circular inner edge secured between the stent and the valve member and an outer edge that extends outward adjacent and to an inflow side of the sealing ring and radially outward beyond the sealing ring. The flap of fabric may have an undulating outer edge which forms a series of outwardly-protruding lobes around its circumference. The outer edge preferably extends outward beyond the sealing ring by between about 10-20% of the diameter of the valve member. In one embodiment, the annular support structure of the valve member includes three evenly-spaced commissure posts alternating with three arcuate cusps, and there are three outwardly-protruding lobes each centered about one of the commissure posts. The outwardly-protruding lobes each may extend outward beyond the sealing ring by between about 10-20% of the diameter of the valve member. The inner edge of the flap of fabric may extend downward within the expandable stent and be secured thereto with sutures. The outer edge may also be intermittently secured to the sealing ring with sutures so as to form the pockets between the sutures.

A third sealing solution comprises a strip of fabric circumscribing the stent outside of the thin fabric having a series of longitudinal pleats formed by folding the strip of fabric longitudinally upon itself at regular intervals to form longitudinal folds and securing the folds with suture to form the pleats. A plush fabric cuff may surround the thin fabric around the inflow edge of the expandable stent, wherein the strip of fabric is located immediately above the plush fabric cuff. The strip of fabric may alternatively extend the entire length of the expandable stent. In a preferred embodiment, the strip of fabric comprises a rectangular strip having a series of tabs spaced intermittently along an upper edge, wherein the rectangular strip is folded upon itself in a manner that places the tabs adjacent one another, wherein the tabs are sewn together and the strip sewn to the outside of the thin fabric to form the pleated skirt.

A further embodiment of the sealing structure comprises a compressible O-ring circumscribing the stent, which may be outside of the thin fabric located at a junction between the sealing ring and the stent. The O-ring may be positioned just below the sealing ring, at the inflow edge of the stent or outside of the band. The O-ring may have an inner core of elastomeric material surrounded by a fabric outer, or may comprise solely of fabric.

A still further embodiment of the sealing structure is a cover of plush fabric circumscribing the stent outside of the thin fabric layer, wherein the cover circumscribes the inflow edge of the stent and extends upward to an upper edge that undulates. The upper edge may extend up to the sealing ring to peaks at evenly-spaced locations and dips down away from the sealing ring in between the peaks. The annular support structure of the valve member may include three evenly-spaced commissure posts alternating with three arcuate cusps, and the peaks align with the commissure posts.

Another embodiment of the sealing structure comprises a cover of plush fabric circumscribing the stent outside of the thin fabric layer, the cover surrounding the entire stent. A narrow band of plush fabric may also circumscribe the cover and be positioned at the inflow edge of the stent or just below the sealing ring.

A still further embodiment of the sealing structure comprises a cover of plush fabric circumscribing the stent outside of the thin fabric layer, the cover surrounding the entire stent and having a tapered radial cross-section with a thicker lower end than an upper end. The tapered radial cross-section may have a linear or non-linear taper, and have a flared lower end.

A still further embodiment of the sealing structure comprises an interrupted band of plush fabric patches circumscribing the lower of the stent. The patches may be rectangular and there may be a plurality of circumferential rows of patches. In one embodiment, there are a plurality of circumferential rows of patches with patches in adjacent rows being vertically offset so as to form a checkered pattern.

Another embodiment of the sealing structure comprises an interrupted band of plush fabric patches circumscribing the inflow edge of the stent. The annular support structure of the valve member may include three evenly-spaced commissure posts alternating with three arcuate cusps, and there are three thicker regions of the sealing ring aligned with the cusps or commissure posts. The sealing ring may extend further downward toward the inflow edge of the stent in the thicker regions. In one embodiment, the thicker regions extend 1.5 or two times further downward toward the inflow edge of the stent than regions between the thicker regions. The thicker regions may extend downward 50% of the vertical height of the stent.

A still further embodiment of the sealing structure comprises a foam strip circumscribing the stent outside of the thin fabric layer. In addition, a narrow band of plush fabric may be attached outward of the foam strip. The foam strip may be surrounded by a second fabric cover or a smooth bioresorbable coating. In one embodiment, the foam strip is a viscoelastic polyurethane foam. In one embodiment, the foam strip is positioned at the inflow edge of the stent.

A still further embodiment of the sealing structure comprises a hydrophilic swellable band circumscribing the stent outside of the thin fabric layer. The swellable band may also be surrounded by a fabric cover. The swellable band may extend an entire height of the stent or only a majority of a height of the stent.

In another embodiment, the sealing structure comprises a layer of bioprosthetic tissue covering the stent outside of the thin fabric layer. Or, a layer of tissue adhesive may cover the stent outside of the thin fabric layer. A layer of foam may be impregnated into the thin fabric layer, the foam being configured to expand upon illumination with UV light. Further, the stent frame may be being covered by a thin fabric layer configured to lengthen beyond the inflow edge of the stent. Another embodiment is a layer of stretchy fabric coiled around the thin fabric layer of the stent and held in place under tension around the stent with fasteners such as sutures or clips, the layer of stretchy fabric forming bunches when the fasteners are removed.

Finally, in any of these embodiments, the sealing ring may be hollow and having a fill valve thereon.

A still further aspect of the application is a method of implanting a hybrid prosthetic heart valve at an atrioventricular heart valve annulus, comprising first providing a hybrid prosthetic heart valve. The heart valve comprises any of the previously described valves with or without the various sealing structures. The method includes advancing the hybrid prosthetic heart valve to a native annulus and positioning the stent in a ventricle adjacent the atrioventricular heart valve annulus, introducing a curable sealing medium between the stent and surrounding ventricular tissue, outwardly expanding the stent against the surrounding ventricular tissue so as to sandwich the curable sealing medium therebetween, exposing the curable sealing medium to light to cure the medium. The step of exposing may include illuminating one or more curing lights within the stent. Preferably, there are a plurality of the curing lights mounted in series on an elongated instrument. The curable sealing medium may be a glycerin- or a gelatin-based tissue glue.

Another method of implanting a hybrid prosthetic heart valve at an atrioventricular heart valve annulus, comprising first providing a hybrid prosthetic heart valve. The heart valve comprises any of the previously described valves with or without the various sealing structures. The method includes securing a precursor band within a ventricle adjacent the atrioventricular heart valve annulus, advancing the hybrid prosthetic heart valve to a native annulus and positioning the stent within the precursor band, and outwardly expanding the stent against the surrounding precursor band. The precursor band may have a series of self-adhesive outer patches configured to attach to surrounding ventricular tissue. The inner circumference of the precursor band may have a series of patches having miniature hooks to which the thin fabric layer of the stent attaches.

A further understanding of the nature and advantages of the present disclosure are set forth in the following description and claims, particularly when considered in conjunction with the accompanying drawings in which like parts bear like reference numerals.

BRIEF DESCRIPTION OF THE DRAWINGS

Certain embodiments will now be explained and other advantages and features will appear with reference to the accompanying schematic drawings wherein:

FIG. 1A is a side view of a hybrid prosthetic heart valve of the prior art, while FIG. 1B shows an anchoring stent therefor with a valve member in phantom, and FIG. 1C is a perspective view of the prosthetic heart valve with portions cutaway to reveal internal structural leaflet supports;

FIG. 5A is an elevational view of a hybrid heart valve of the present application having a multi-layered sealing assembly including a row of inflatable pockets, while FIGS. 5B and 5C are vertical sectional views through the heart valve showing a strip of material that forms pockets that fill with blood for better sealing;

FIG. 5D is a laid-out plan view of a strip of fabric used to form the pockets in the heart valve of FIG. 5A, and FIG. 5E shows the strip of fabric after being folded in half for attachment around the expandable anchoring stent;

FIG. 11A is a top plan view of another hybrid heart valve having a loose fabric flap positioned directly under a sealing ring around a non-expandable valve member, while

FIG. 12A is an elevational view of a hybrid heart valve where a plush fabric layer with an undulating upper edge is fastened over a fabric-covered anchoring stent, and FIG. 12B is a vertical sectional view through a cusp portion of the heart valve;

FIG. 13A is an elevational view of a hybrid heart valve where two plush fabric layers of different size are attached over a fabric-covered anchoring stent, and FIG. 13B is a vertical sectional view through a cusp portion of the heart valve;

FIG. 16A is an elevational view of a hybrid heart valve where a lower plush fabric cuff is provided over a fabric-covered anchoring stent, and where a sealing ring around a non-expandable valve member is enlarged and has cusp bulges, and FIG. 16B is a vertical sectional view through a cusp portion of the heart valve;

FIG. 17A is an elevational view of a hybrid heart valve having a lower plush fabric cuff over a fabric-covered anchoring stent, where a sealing ring around a non-expandable valve member is enlarged and has commissure bulges, and FIGS. 17B and 17C are vertical sectional views through a commissure portion of the heart valve adjacent a target annulus while being deployed;

FIG. 22A is an elevational view of a hybrid heart valve with a fabric-covered anchoring stent around which is provided a hydrophilic swellable band, and FIG. 22B is a partial cutaway and sectional view showing the band after swelling;

FIG. 23A is an elevational view of a hybrid heart valve with a fabric-covered anchoring stent around which is provided a fabric-covered foam band around a lower end thereof, and FIG. 23B is a vertical sectional view through a cusp portion of the heart valve;

FIGS. 26A and 26B are perspective views of an assembly of a hybrid heart valve having a stretched fabric layer attached over a fabric-covered anchoring stent, and FIG. 26C shows the assembled valve after tension in the stretched fabric layer has been released to create bunches in the layer;

FIG. 27A is an elevational view of a hybrid heart valve having a fabric-covered anchoring stent and an inflatable sealing ring around a non-expandable valve member, while FIGS. 27B and 27C are vertical sectional views through a cusp portion of the heart valve showing inflation of the sealing ring with a hydrogel;

FIGS. 28A-28C are vertical sectional views through a hybrid heart valve illustrating a procedure for introducing a curable sealing medium between a fabric-covered anchoring stent and a target annulus while being deployed; and FIGS. 29A-29C are perspective views of a procedure for implanting a hybrid heart valve within a self-adhesive precursor band secured just below the annulus.

DETAILED DESCRIPTION OF CERTAIN EMBODIMENTS

Figure 1:
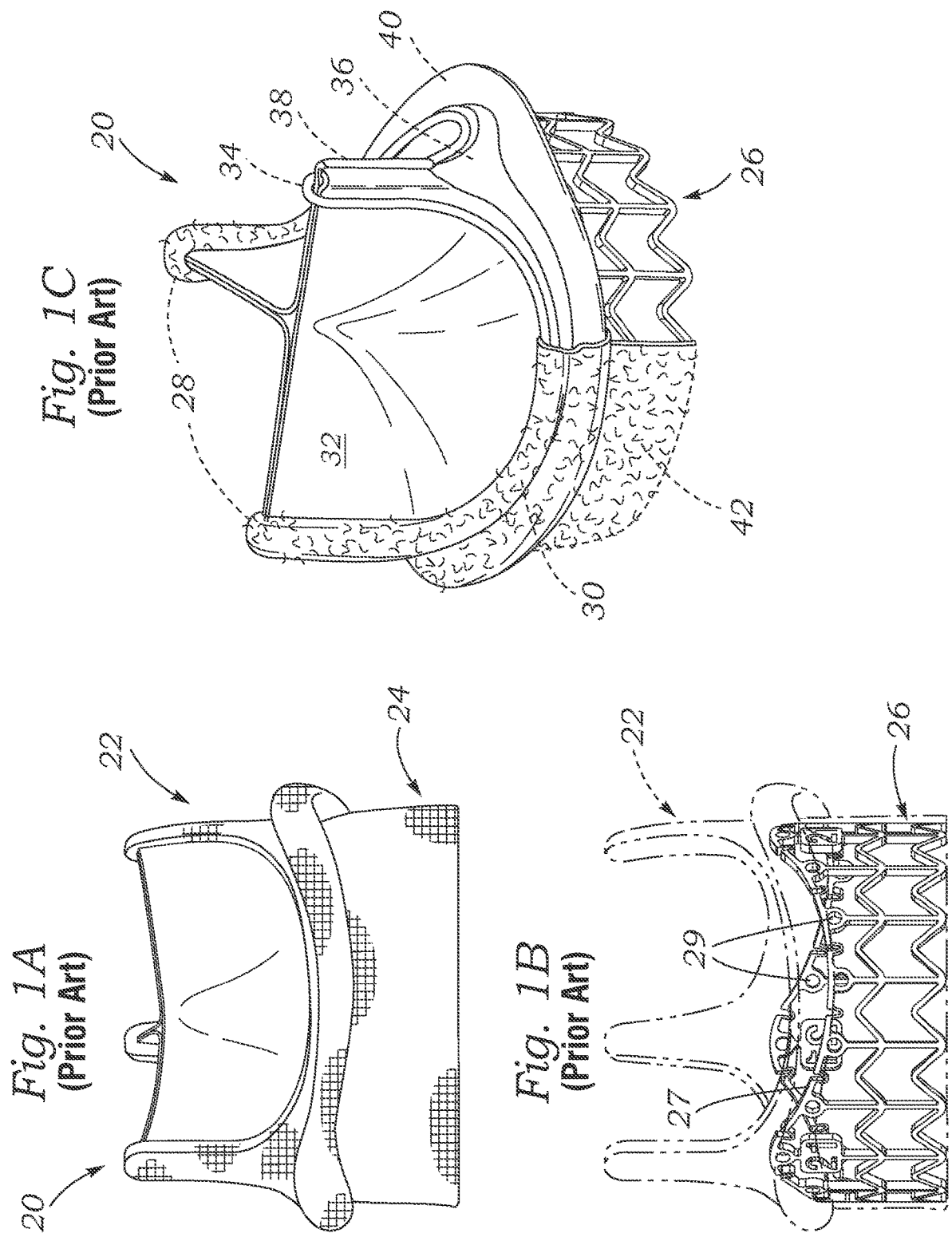

Certain embodiments attempt to overcome drawbacks associated with conventional, open-heart surgery, while also adopting some of the techniques of newer technologies which decrease the duration of the treatment procedure. The prosthetic heart valves of the present disclosure are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (e.g., naked eye) visualization of the heart valve annulus. In addition, it will be recognized that embodiments of the prosthetic heart valves described herein may also be configured for delivery using percutaneous approaches, and those minimally-invasive surgical approaches that require remote implantation of the valve using indirect visualization. However, the latter two approaches—percutaneous and minimally-invasive—invariably rely on collapsible/expandable valve constructs. And, while certain aspects described herein could be useful for such valves and techniques, the primary focus and main advantages of the present application is in the realm of non-expandable "surgical" valves introduced in conventional manners.

One primary focus of the present disclosure is a "hybrid" prosthetic heart valve in which a tissue anchor is implanted at the same time as a surgical valve member resulting in certain advantages. The exemplary unitary prosthetic heart valve of the present disclosure is a hybrid valve member, if you will, with both non-expandable and expandable portions. By utilizing an expandable anchoring skirt or stent coupled to a (surgical) non-expandable valve member, the duration of the anchoring operation is greatly reduced as compared with a conventional sewing procedure utilizing an array of sutures. The expandable anchoring stent may simply be radially expanded outward into contact with the implantation site, or may be provided with additional anchoring means, such as barbs. As stated, conventional open-heart approach and cardiopulmonary bypass familiar to cardiac surgeons are used. However, due to the expandable anchoring stent, the time on bypass is greatly reduced by the relative speed of implant in contrast to the previous time-consuming knot-tying process.

For definitional purposes, the terms "stent," "stent frame" or "coupling stent" refer to a structural component that is capable of anchoring to tissue of a heart valve annulus. The coupling stents described herein are most typically tubular stents, or annular stents having varying shapes or diameters. A stent is normally formed of a biocompatible metal frame, such as stainless steel or Nitinol. More preferably, in the context of the present disclosure the stents are made from laser-cut tubing of a plastically-expandable metal. Other coupling stents that could be used with valves of the present disclosure include rigid rings, spirally-wound tubes, and other such tubes that fit tightly within a valve annulus and define an orifice therethrough for the passage of blood.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a contracted to an expanded diameter. It should be understood that the term balloon-expanding stents encompasses plastically-expandable stents, whether or not a balloon is used to actually expand it (e.g., a device with mechanical fingers could expand the stent). The material of the stent plastically deforms after application of a deformation force such as an inflating balloon or expanding mechanical fingers. Consequently, the term "balloon-expandable stent" should be understood as referring to the material or type of the stent as opposed to the specific expansion means. Unless expressly limited by a particular claim, the term stent or stent frame may be self- or balloon-expandable.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients. In a preferred embodiment, the non-expandable valve member is an "off-the-shelf" standard surgical valve of the type that has been successfully implanted using sutures for many years, such as the Carpentier-Edwards PERIMOUNT Magna® Aortic Heart Valve available from Edwards Lifesciences of Irvine, California, though the autonomous nature of the valve member is not absolutely required. In another embodiment, the valve member comprises a PERIMOUNT Magna® Aortic valve subjected to GLX tissue treatment, which allows for dry packaging and sterilization and eliminates the need to rinse the valves before implantation. In this sense, a "off-the-shelf" prosthetic heart valve is suitable for stand-alone sale and use, typically including a non-expandable, non-collapsible support structure having a sewing ring capable of being implanted using sutures through the sewing ring in an open-heart, surgical procedure.

A primary focus of the present disclosure is a prosthetic heart valve having a single stage implantation in which a surgeon secures a hybrid valve having an anchoring stent and valve member to a valve annulus as one unit or piece (e.g., a "unitary" valve). Certain features of the hybrid anchoring stent and valve member are described in U.S. Pat. No. 8,641,757, filed Jun. 23, 2011, the contents of which are expressly incorporated herein. The valves described herein are especially beneficial in a single stage implant procedure, but that does not necessarily limit the overall system to just one part. For instance, the heart valves disclosed herein could also use a base stent or ring followed by implant of a hybrid heart valve. Because the hybrid heart valve preferably has a non-expandable and non-collapsible valve member annular support structure, and a plastically-expandable anchoring stent, it effectively resists recoil of a self-expanded base stent.

As a point of further definition, the term "non-expandable" is used herein to refer to a component of the heart valve that is incapable of expanding from a first, delivery diameter to a second, implantation diameter. However, a non-expandable structure might undergo slight expansion or transient flexing from a rise in temperature, or other such incidental cause such as fluid dynamics acting on leaflets or commissures. Likewise, "non-expandable" does not mean that the implanted valve is incapable of further expansion, as some newer surgical heart valves are capable of post-implant expansion in a so-called valve-in-valve procedure. Typically, a dilation force such as with a balloon must be applied to expand such valves post-implant. Stated another way, "non-expandable" means the valve is not suitable for percutaneous or minimally-invasive deliveries, and must thus be implanted surgically. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present disclosure are particularly advantageous for one implantation site or the other, in particular, the aortic annulus. However, unless the combination is structurally impossible, or excluded by claim language, any of the heart valve embodiments described herein could be implanted in any body channel.

Furthermore, though valve introduction downward through an aorta into position at the aortic annulus is illustrated, the reverse is also contemplated in a transapical procedure, for example. The same goes for the other valve annuluses.

FIG. 1A is a side view of a hybrid prosthetic heart valve 20 of the prior art, which includes an upper non-expandable valve member 22 coupled to a cloth-covered anchoring stent 24. FIG. 1B shows the valve member 22 in phantom to illustrate the contours of an expandable frame 26 of the anchoring stent 24, and FIG. 1C is a perspective view of the entire heart valve 20 with portions at one commissure post 28 cutaway to reveal internal structural leaflet supports.

In all of the views herein the heart valves are shown in an upright orientation with the flow axis aligned vertically. For the purpose of nomenclature, blood flows upward through the valves such that a lower end corresponds to an inflow or inlet end and an upper end corresponds to an outflow or outlet end. Of course, during implant and thereafter the heart valves are not necessarily so vertically oriented.

The valve member 22 of the hybrid prosthetic heart valve 20 has an inner support structure including three upstanding commissure posts 28 alternating with three arcuate cusps 30 curving in an inflow direction. Three flexible leaflets 32 are supported by the commissure posts 28 and cusps 30 and extend across a generally cylindrical flow orifice defined therewithin. The leaflets 32 are attached to an up and down undulating typically metallic wireform 34 defining cusps and commissures via a cloth covering. The upstanding posts 36 rise up adjacent to and just outside of the commissures of the wireform 34, and outer tabs 38 of the leaflets 32 extend underneath the wireform, wrap around the posts, and are secured thereto with sutures.

In the illustrated embodiment, the heart valve 20 also includes a highly compliant sealing ring 40 extending outward therefrom at approximately the interface between the valve member 22 and the anchoring stent 24. The sealing ring 40 as well as the expandable frame 26 are covered with a thin fabric 42 that helps prevent leakage around the outside of the valve once implanted. Furthermore, the sealing ring 40 is also suture-permeable and may be used to secure the valve in place in the native annulus. Typically, the sealing ring 40 has an inner elastomeric (e.g., silicone) sponge or core covered with a polymer fabric, but may also be folded or rolled fabric.

The expandable frame 26 is preferably formed by a series of circumferential and axial or angled struts and has an undulating or scalloped upper strut 27. The stent frame 26 assembles within a tubular section of thin fabric 42 which is then drawn taut, inside and out, and sewn thereto to form the cloth-covered anchoring stent 24. The anchoring stent 24 attaches to an inflow (lower) end of the inner support structure of the valve member 24, typically using sutures connected between fabric that covers both elements. More specifically, the anchoring stent 24 preferably attaches to the valve member 22 during the manufacturing process in a way that prevents reduction of the valve's effective orifice area (EOA). In this regard, sutures may be passed through apertures or eyelets 29 arrayed along the upper or first end 27 of the expandable frame 26 and then through fabric surrounding components within the prosthetic valve member 22. Other connection solutions include prongs or hooks extending inward from the stent, ties, hook-and-loop, snaps, adhesives, etc.

Figure 2:
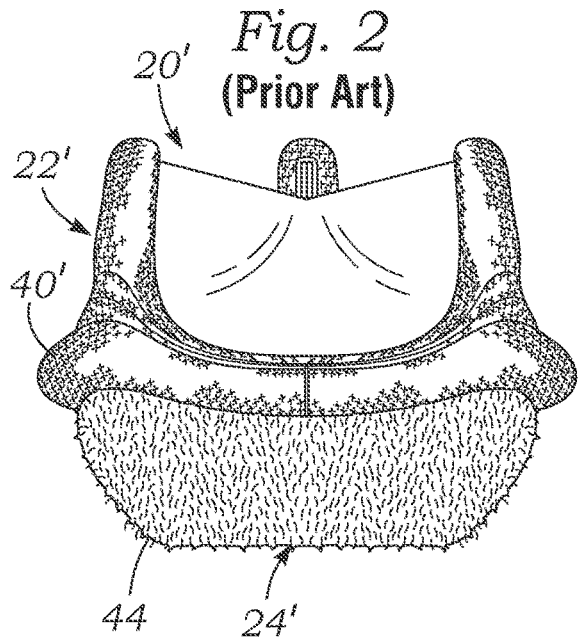
FIG. 2 is an elevational view of a hybrid prosthetic heart valve of the prior art showing a lower expandable anchoring stent covered with a plush sealing fabric.
Figure 3A:
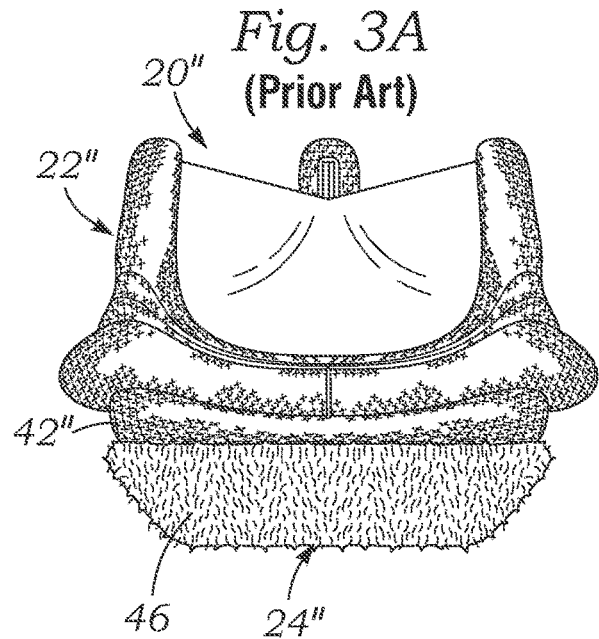
FIGS. 3A and 3B are elevational and perspective views of another hybrid heart valve of the prior art having a lower expandable anchoring stent shown contracted and expanded, respectively, the stent being covered first with a flat fabric layer and then with a plush sealing fabric over a lower portion.

It should be noted that FIG. 1B shows the stent frame 26 in a tubular, uncrimped state. During process of attaching the thin fabric 42, the stent frame 26 may remain tubular, and later the frame will be crimped toward an inflow edge opposite the scalloped upper end 27 into a conical delivery configuration as seen in FIGS. 2 and 3A. Of course, the frame 26 may be crimped first and then covered with fabric. Expansion of the stent 24 causes the inflow edge to expand while the opposite edge that is secured to the valve member 22 remains generally unchanged in circumference, so that the implanted configuration as seen in FIG. 3B is again conical but flared outward. The general function of the anchoring stent 24 is to provide the means to attach the prosthetic valve member 22 to the native aortic root. This attachment method is intended as an alternative to the present standard surgical method of suturing aortic valve bio-prostheses to the aortic valve annulus with multiple suture loops passed through the sealing ring 40, and is accomplished in much less time. Further, this attachment method improves ease of use by eliminating most if not all suturing. The expandable frame 26 may be a pre-crimped, tapered, 316L stainless steel balloon-expandable stent, desirably covered by the thin fabric 42, preferably polyester, to help seal against paravalvular leakage and promote tissue ingrowth once implanted within the annulus. However, the expandable frame 26 may alternatively be self-expanding and the sealing solutions described herein are not limited to one type of frame or another unless stated in particular claims.

The completed valve member 22 provides the occluding surfaces for the prosthetic heart valve 20, preferably in the form of flexible bioprosthetic leaflets. For example, the valve leaflets may be taken from another human heart (cadaver), a cow (bovine), a pig (porcine valve) or a horse (equine). Alternatively, the valve member may comprise mechanical components rather than biological tissue. Although an autonomous (e.g., capable of stand-alone surgical implant) flexible leaflet valve member 22 is described and illustrated, alternative valve members that have rigid leaflets, or are not fully autonomous may be substituted.

For bioprosthetic valves, an exemplary process includes storing the prosthetic heart valve 20 in a preservative solution after manufacture and prior to use. A preservative such as glutaraldehyde is provided within a storage jar. This "wet" storage arrangement applies to the illustrated heart valve 20 shown, which includes conventional bioprosthetic leaflets. However, as mentioned above, the heart valve could also be used without a preservative solution for bioprosthetic leaflets that can be dry packaged, such as with the RESILIA® tissue from Edwards Lifesciences, and also for mechanical valves.

FIG. 2 is an elevational view of another hybrid prosthetic heart valve 20' of the prior art showing a lower expandable anchoring stent 24' covered with an outer sealing layer of plush fabric 44. (The heart valve 20' may be constructed the same as the heart valve 20 of FIGS. 1A-1C, and thus like elements will be given like numbers with a prime (') designation.) The layer of plush fabric 44 entirely covers the fabric-covered anchoring stent 24', extending to an undulating upper end just below the sealing ring 40'.

The material of the layer of plush fabric 44 may vary, but preferably provides a compressible buffer around the anchoring stent 24. The main functions of the fabric layers covering the stent 24' are to help prevent paravalvular leaks and provide means to securely encapsulate any Calcium nodules on the aortic valve leaflets (if left in place) and/or the aortic valve annulus. Covering the entire anchoring stent 24' eliminates exposed metal and decreases the risk of thromboembolic events and abrasion.

In the present application, the term "thin" or "flat" fabric refers to any number of biocompatible fabrics used in surgical implants, such as polytetrafluoroethylene (PTFE) cloth, e.g., TEFLON® PTFE (DuPont), although other biocompatible fabrics may be used. More particularly, the thin fabric is a PTFE flat yarn obtained from Atex Technologies Inc. of Pinebluff, NC The thickness of the thin fabric is desirably about 0.5 mm.

The term "plush," "fuzzy" or "fluffy" layer or fabric refers to a much thicker material to provide enhanced prevention of paravalvular leakage. For instance, the plush layer is formed of polyethylene terephthalate (PET) in a single layer or multiple layers, PTFE (TEFLON® PTFE), a silicone ring covered by fabric, or other similar expedients. More preferably, a plush fabric disclosed herein has a base yarn which is flat yarn 40/27, and a loop yarn extending therefrom made from PET 70/12 textured yarn both obtained from Atex Technologies Inc. of Pinebluff, NC The thickness of the plush layer is desirably about 1.2 mm or more, uncompressed, while the thickness of the thin fabric may be 50% or less of that. In alternative embodiments, different materials can be used for assemblies of the thin fabric and the plush layer, such as PTFE/cloth, PTFE/PET, cloth/cloth, or PTFE or cloth for the thin fabric and a swellable hydrophilic polymer such as an acrylic for the plush layer. In another embodiment, opposite sides of a strip of plush fabric are used to create a sealing flange on the expandable anchoring stent 24. The material of the strip includes a relatively smooth side with rows of ribs of the fabric weave, and a plush or relatively fluffy side with outwardly projecting loops and loose threads of the polymer material. The strip is mounted on the anchoring stent 24 with the fluffy side out, or is sewn into a tube with the fluffy side outward and then flattened into a strip and attached to the stent.

Figure 3B:
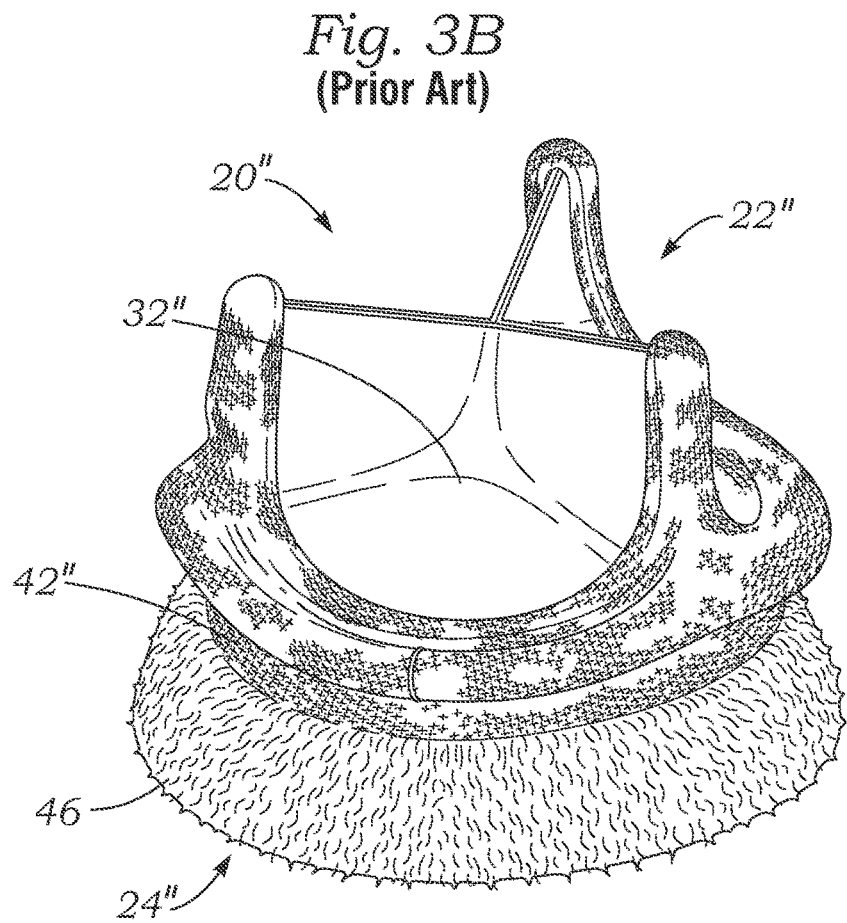

FIGS. 3A and 3B are elevational and perspective views of another hybrid heart valve 20" of the prior art having a lower expandable anchoring stent 24" shown contracted and expanded, respectively, the stent being covered first with a flat fabric layer 42" and then with a band of plush sealing fabric 46 over a lower portion.

In a preferred embodiment, the band of plush fabric 46 has an axial dimension of between about 2-5 mm, and is spaced from the upper end of the expandable frame by a distance that varies between about 2-5 mm. The lower end of the expandable frame may also be scalloped to follow the upper end, in which case the band of plush fabric 46 may also undulate to maintain an even distance with the upper end. If a knitted PET fabric is used, the band of plush fabric 46 desirably has a radial thickness of at least twice the thickness of the underlying flat fabric layer 42".

The plush fabric 46 over the flat fabric layer 42" provides a secondary sealing structure around the frame 26 of the stent 24" which enhances leak prevention. The present application provides a number of other secondary sealing structures that may be utilized and are believed superior to the plush fabric 46 in FIG. 3A.

Figure 4B:
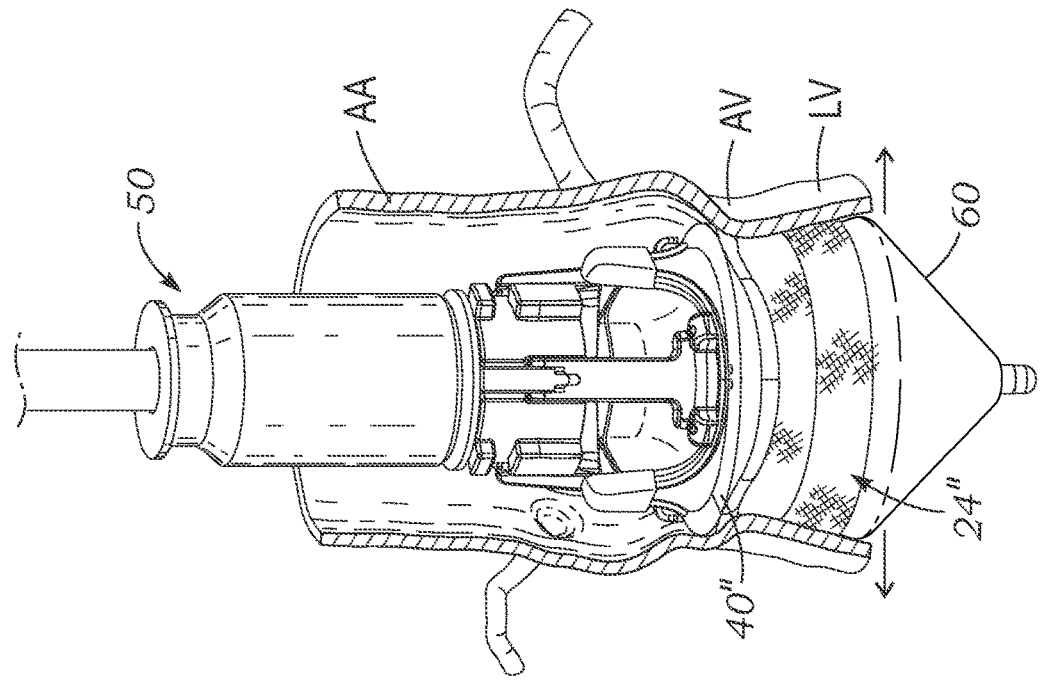
FIG. 4B shows a balloon of a balloon catheter of the delivery system inflated to expand the anchoring stent.
Figure 4A:
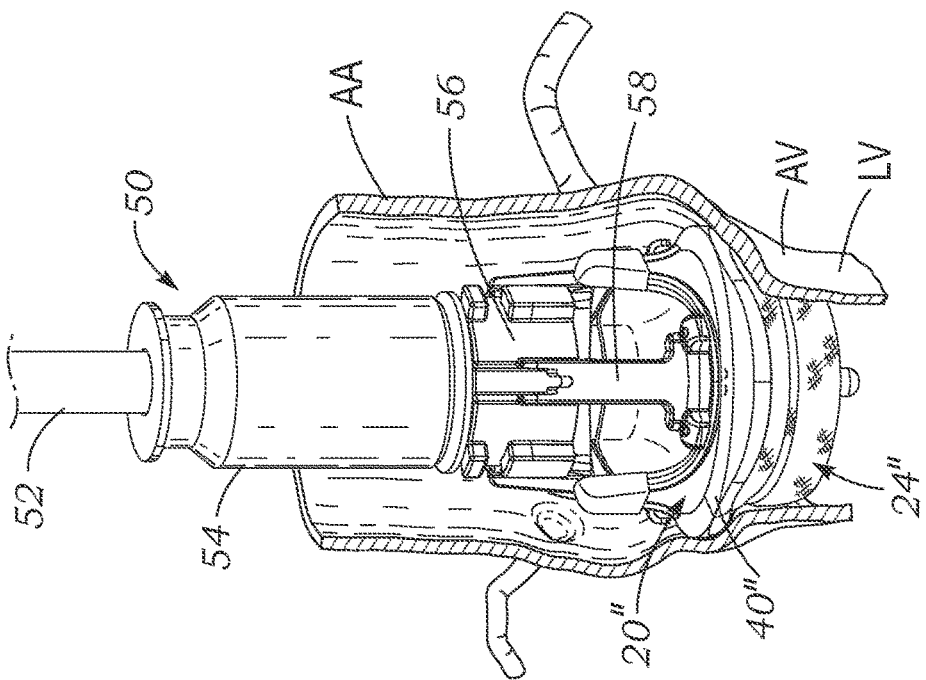
FIG. 4A is a perspective cutaway view of an aortic annulus showing a portion of the adjacent left ventricle below the ascending aorta, illustrating a hybrid heart valve mounted on a distal section of a prior art delivery system advanced into position within the aortic annulus with an anchoring stent located in the left ventricle.

FIG. 4A is a perspective cutaway view of a native aortic valve AV between a portion of the adjacent left ventricle LV below the ascending aorta AA. The hybrid heart valve 20" mounts on a distal end of a delivery system 50 advanced into position within the aortic valve annulus with the anchoring stent 24" located in the left ventricle LV. The delivery system may include an elongated malleable handle shaft 52 terminating in a generally tubular adapter 54 that couples to a valve holder 56 secured to the valve 20" with sutures, for example, between lower ends of three legs 58 of the valve holder 56 and the sealing ring 40" of the valve. Further details of an exemplary delivery system 50 may be seen in U.S. Pat. No. 8,641,757, filed Jun. 23, 2011.

FIG. 4B shows a balloon 60 of a balloon catheter (not shown) of the delivery system inflated to expand the anchoring stent 24". The balloon catheter advances linearly through the handle shaft 52, adapter 54, and valve holder 56 into position within the stent 24". The delivery system 50 preferably provides binary position displacement of the balloon 60, either retracted substantially within the handle shaft 52 or advanced precisely as far as necessary to expand the anchoring stent 24" of the prosthetic heart valve 20". The balloon 60 desirably has a frustoconical profile that expands the anchoring stent 24" into a frustoconical expanded state. Not only does this conform better to the subannular contours but over expands somewhat the annulus that a larger valve may be utilized then without the expansion.

An implant procedure involves delivering the heart valve 20" and expanding the anchoring stent 24" at the aortic annulus. Because the valve member of the heart valve 20" is non-expandable, the entire procedure is typically done using the conventional open-heart technique. However, because the anchoring stent 24" is implanted by simple expansion, with reduced suturing, the entire operation takes less time. This hybrid approach will also be much more comfortable to surgeons familiar with the open-heart procedures and commercially available heart valves. Moreover, the relatively small change in procedure coupled with the use of proven heart valves should create a much easier regulatory path than strictly expandable, remote procedures. Even if the system must be validated through clinical testing to satisfy the Pre-Market Approval (PMA) process with the FDA (as opposed to a 510(k) submission), at least the surgeon acceptance of the quick-connect heart valve 20 will be greatly streamlined with a commercial heart valve that is already proven, such as the Magna® Aortic Heart Valve from Edwards Life sciences.

The following disclosure presents a variety of sealing solutions for preventing or reducing paravalvular leakage around a hybrid heart valve, and in particular around its expandable anchoring stent 24 and especially between the sealing ring 40 and the expandable anchoring stent. It should be understood that unless prevented by mutual exclusivity or as stated, the various solutions described herein may be combined in other ways to result in different configurations, and the scope of the disclosure should not be therefore limited to the explicit embodiments shown. For the sake of uniformity, the components of the prior art hybrid heart valve 20 aside from the elements for sealing around the anchoring stent 24 will be given like numbers as described above. These include: heart valve 20, valve member 22, anchoring stent 24, expandable frame 26, valve commissures 28, valve cusps 30, leaflets 32, wireform 34, inner stent 36, leaflets 38, sealing ring 40, and thin fabric 42 around the expandable stent.

Fluid Pockets

FIG. 5A is an elevational view of a first hybrid heart valve 20 having a multi-layered sealing assembly including a row of inflatable pockets 70, while FIGS. 5B and 5C are vertical sectional views through the heart valve showing the pockets that fill with blood for better sealing. The expandable frame 26 of the anchoring stent 24 is first covered inside and out by a layer of thin fabric 42. A relatively narrow band or cuff of plush fabric 72 attaches around an inflow end of the stent 24 over the top of the thin fabric 42. As seen in FIGS. 5B and 5C, the plush fabric cuff 72 is formed by a strip of material folded over to double its thickness. The pockets 70 are located in a relatively narrow band also attached over the top of the thin fabric 42 and just below the sealing ring 40. The pockets 70 help reduce paravalvular leakage between the sealing ring 40 and the expandable anchoring stent 24.

FIG. 5D is a laid-out plan view of an elongated strip 74 of fabric used to form the pockets 70 in the heart valve of FIG. 5A. The strip 74 is desirably formed of a thin fabric, such as the same PTFE material used for the thin fabric 42. The strip 74 includes a rectangular lower portion 76 separated from a crenellated or undulating upper portion 78 at a longitudinal fold line 80. In this regard, "crenellated" means having peaks and valleys formed by a series of concave and convex curves. FIG. 5E shows the strip of fabric after being folded in half along the fold line 80 for attachment around the expandable anchoring stent. More specifically, the lower portion 76 is folded behind the upper portion 78. The folded strip 74 is then attached around the circumference of the thin fabric 42 using sutures 82 or the like. The sutures 82 are positioned along a lower edge of the strip 74 as well as at the peaks of the crenellated upper edge of the upper portion 78 such that the valleys are left unattached. A single line of sutures 84 across the crenellated upper edge of the upper portion 78 and through the folded-over lower edge of the strip 74 may also be used for convenience. Although the upper edge of the upper portion 78 of the strip 74 is shown crenellated, it may also be linear with only intermittent portions secured by sutures so as to leave other portions unattached for forming the pockets 70.

FIGS. 5B and 5C extend, respectively, through one of the peaks and one of the valleys of the folded strip 74. FIG. 5C indicates outward expansion of one of the pockets 70 from regurgitant blood flow which may find its way around the heart valve 20 after implantation. That is, the heart valve leaflets 32 are shown closed in FIG. 5A, which in use tends to build up pressure on the outflow side of the valve. This pressure can sometimes force blood around the outside of the valve if there is insufficient paravalvular sealing. Often times, the surrounding anatomy of the native valve annulus and adjacent tissue is highly uneven such that a generally cylindrical prosthetic valve (or conical stent) contacts the anatomy around only portions of its circumference. The pockets 70, in addition to the various layers of fabric, provide an additional barrier preventing blood flow around the valve. The pockets 70 can fill with blood and thus expand where there is a space between the anchoring stent 24 and the surrounding anatomy.

The folded strip 74 is desirably secured around the anchoring stent 24 approximately at an axial midpoint thereof. That is, the folded strip 74 is located in a narrow band above the inflow end of the stent 24, and preferably above the band of plush fabric cuff 72, while also being below the sealing ring 40, which undulates in the illustrated aortic valve. Of course, the location of the folded strip 74 may vary, and it may be enlarged, as will be seen below. In one alternative, the folded strip 74 with pockets 70 is located just below the sealing ring 40 and the plush fabric cuff is enlarged as indicated by the dashed outline 86 so that it reaches and covers the lower edge of the strip.

Figure 6A:
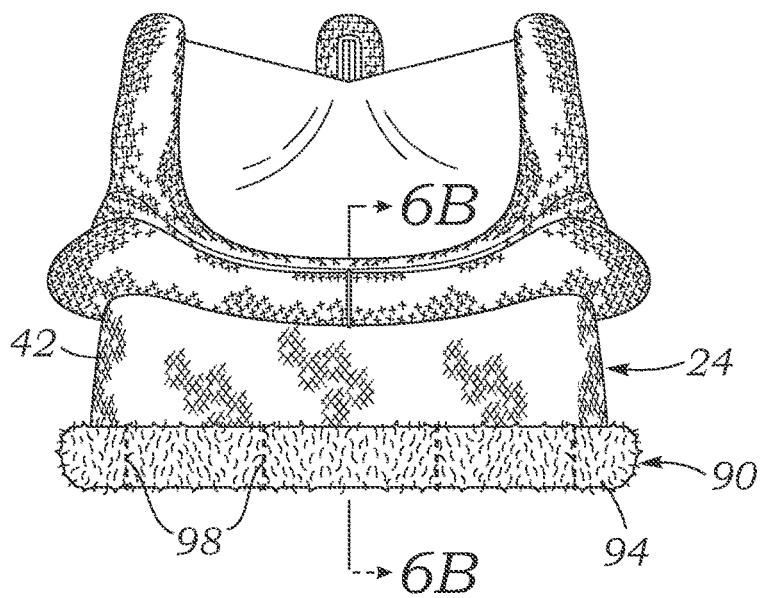
FIG. 6A is an elevational view of a hybrid heart valve where a fabric-covered anchoring stent has a lower sealing flange formed by pockets and plush fabric, while Figure GB is a vertical sectional view through a cusp portion of the heart valve.
Figure 6B:
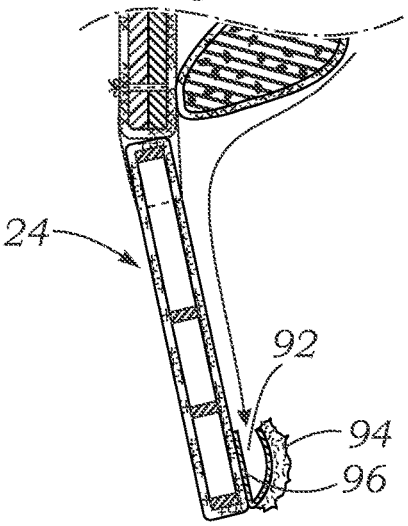

FIG. 6A illustrates a hybrid heart valve where a fabric-covered anchoring stent 24 has a lower sealing cuff or flange 90 formed by pockets 92 and plush fabric 94 on the outside. The anchoring stent 24 once again is covered inside and out by a thin fabric 42. As seen in the vertical sectional view of FIG. 6B, the pockets 92 may be formed by a folded-over strip 96 of fabric, such as described above with respect to the folded strip 74 of FIG. 5A. The strip of plush fabric 94 has approximately the same axial height as the folded over strip 96, both of which are approximately 20-50% of the axial height of the anchoring stent 24. An inner layer of the folded-over strip 96 may be secured around to the anchoring stent 24, while a plurality of circumferentially spaced-apart vertically-aligned seams 98 segregate the strip into the pockets 92. That is, an outer layer of the folded-over strip 96 is only secured to the anchoring stent at the periodic seams 98 such that segments of the upper edge remain loose. As with the pockets described above, regurgitant blood flow around the valve tends to fill the space between the inner and outer layers of the folded over strip 96, such as seen in FIG. 6B. At the same time, the provision of the plush fabric 94 surrounding the strip 96 provides good sealing in areas where the anchoring stent 24 expands outward into intimate contact with the surrounding anatomy.

Figure 7A:
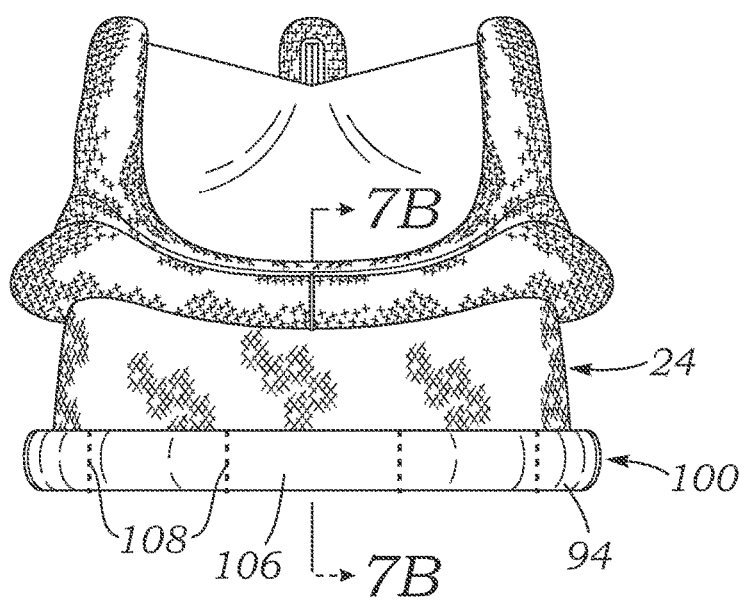
FIG. 7A is an elevational view of a hybrid heart valve where a fabric-covered anchoring stent has a lower sealing flange formed by a strip of plush fabric around which pockets are formed.
Figure 7B:
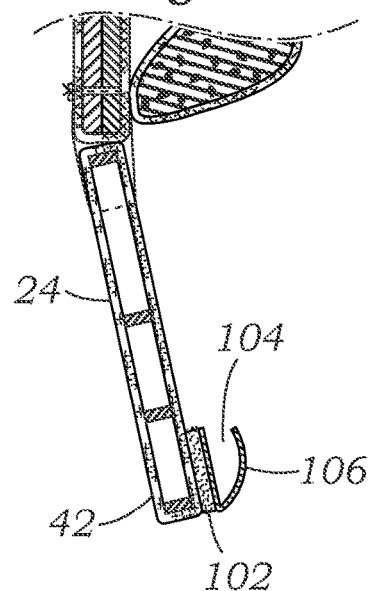
FIG. 7B is a vertical sectional view through a cusp portion of the heart valve.

FIG. 7A is a variation of the hybrid heart valve of FIG. 6A, where a fabric-covered anchoring stent 24 has a lower sealing cuff or flange 100 formed by a strip of plush fabric 102 around which pockets 104 are formed. FIG. 7B is a vertical sectional view through a cusp portion of the heart valve showing the plush fabric 102 secured to a lower end of the outside thin fabric layer 42 around the anchoring stent 24. A folded-over strip 106 of fabric is secured to the outside of the plush fabric 102, and is desirably approximately the same axial height (e.g., about 20-50% of the height of the stent). A series of circumferentially-spaced vertically-oriented seams 108 segment an outer layer of the folded-over strip 106 such that a majority of its upper edge is only periodically connected around the stent. As before, paravalvular leakage around the outside of the valve in areas where the stent 24 is not in close contact with the surrounding anatomy tends to billow out the outer layer of the strip 106 to form the pockets 104. The intermediate layer of the plush fabric 102 between the pockets 104 and the stent 24 provides additional thickness to the sealing flange 100 such that a better conforms to an uneven surrounding anatomy.

Figure 8A:
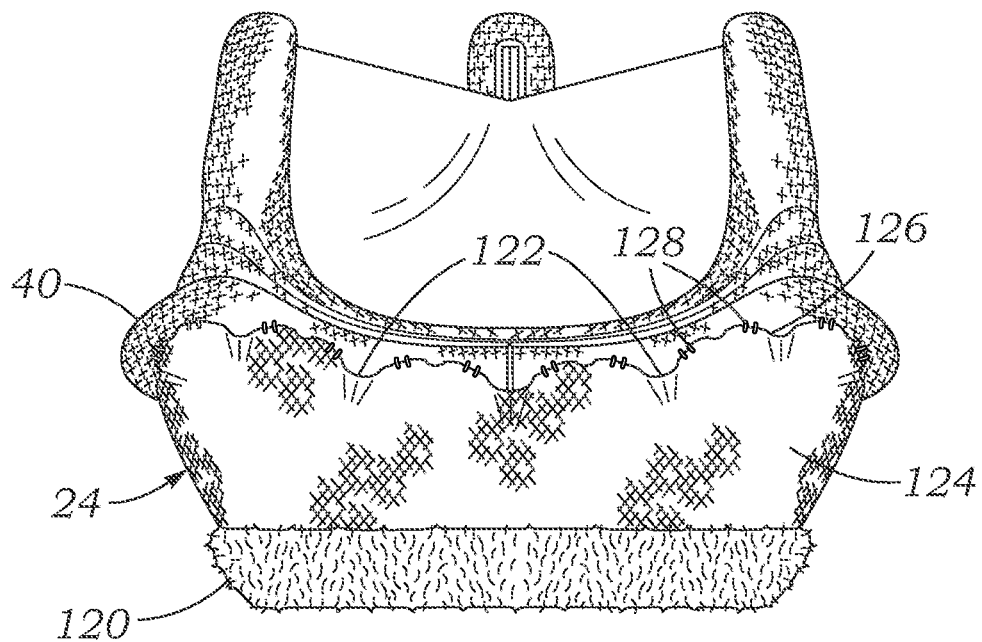
FIG. 8A is an elevational view of a hybrid heart valve having a lower plush sealing cuff on the anchoring stent as well as a series of large sealing pockets covering the remainder of the anchoring stent.

FIG. 8A illustrates another version of a hybrid heart valve having a lower plush sealing cuff 120 combined with pockets 122. Specifically, a lower band of plush fabric 120 is secured to the lower end of the anchoring stent 24. A series of large sealing pockets 122 covers the remainder of the anchoring stent, up to the sealing ring 40. The pockets 122 may be formed by a generally conical sheet 124 of material, such as the same material as the thin fabric 42 covering the stent. Although not shown, a circular lower edge of the sheet 124 is desirably securely attached around the fabric-covered stent 24. Once again, an upper edge 126 may be crenellated or circular. An intermediate circumferential seam (not shown) may also be included to secure the sheet 124 to the stent 24 and reduce the axial height of the pockets 122 thus formed to an upper half of the sheet.

The upper edge 126 of the fabric sheet 124 is secured to the sealing ring 40 at equally spaced intervals, such as at each peak of the crenellated upper edge. A series of spaced-apart sutures 128 at the peaks leave the intermediate portions (in this case each of the valleys) unconnected or loose to form the pockets 122. The sutures 128 may be spaced far apart such as 120° apart, or close together such as 15° apart. Desirably there are at least 3 and no more than 24 pockets 122.

Figure 8B:
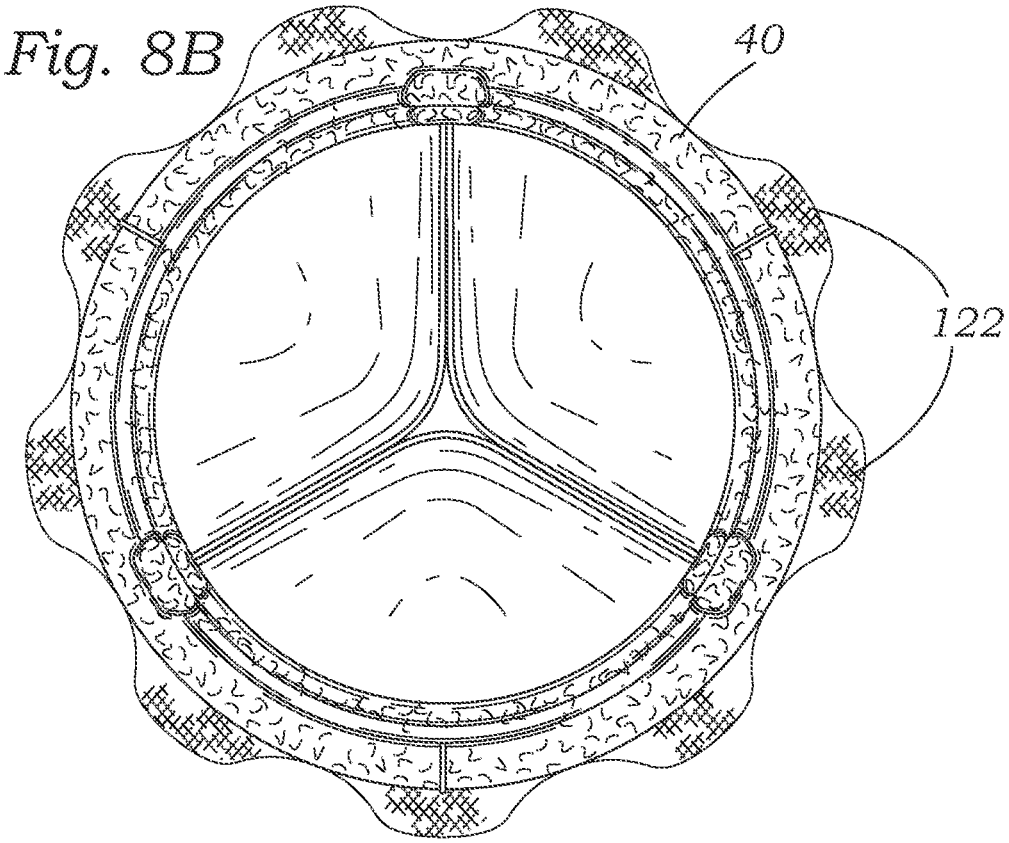
FIG. 8B is a top elevational view of the heart valve showing the large sealing pockets extending outward beyond an upper sealing ring around a non-expandable valve member.

The circumferential dimension of the sheet 124 at the upper edge 126 may be significantly larger than the circumference of the anchoring stent 24 at that elevation such that the material between the space-apart sutures 128 is somewhat bunched or loose. In this regard, the pockets 122 tend to be relatively large, as seen in the top elevational view of FIG. 8B, where the pockets are shown extending radially outward beyond the upper sealing ring 40. This arrangement greatly assists in reducing paravalvular leakage between the sealing ring 40 and the expandable anchoring stent 24. In one embodiment, the sealing cuff 120 extends axially between about 20-50% of the height of the anchoring stent 24, while the sheet 124 of material that forms the pockets 122 extends the remaining height of the stent up to the sealing ring 40. In accordance with the remarks above concerning combining various embodiments, the sealing cuff 120 around the lower portion of the stent 24 may be formed in the manner as shown in FIG. 6A or 7A so as to have pockets as well.

Pleated Skirts

Figure 9A:
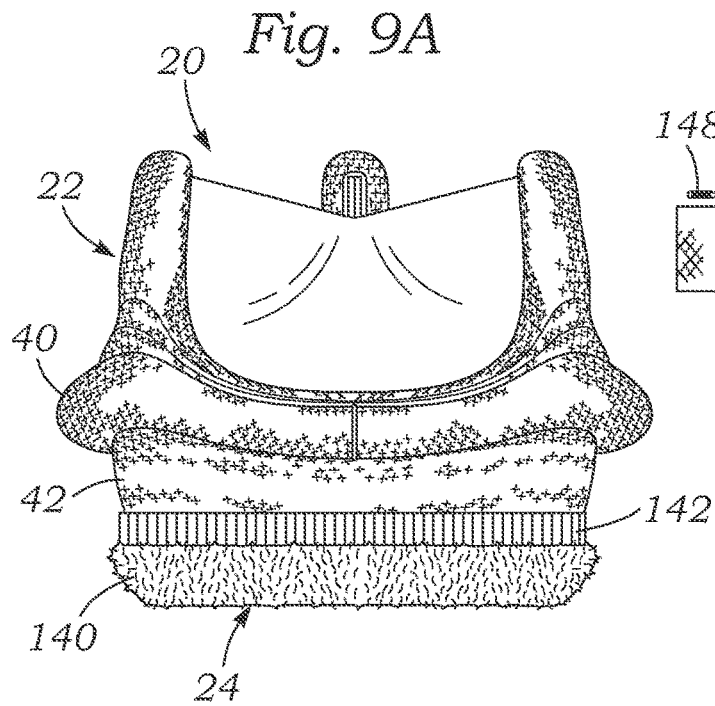
FIG. 9A is an elevational view of a hybrid heart valve where a fabric-covered anchoring stent has a lower plush sealing cuff as well as a band of pleated fabric just above the sealing cuff.
Figure 9B:
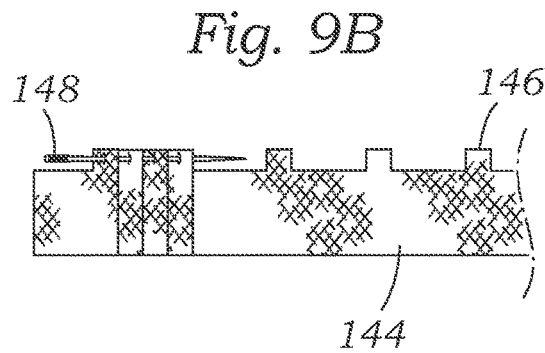
FIG. 9B is a laid-flat plan view of a strip of material and sewing technique used to form the band of pleated fabric.

In FIG. 9A, a hybrid heart valve 20 has a fabric-covered anchoring stent 24 that terminates in a lower plush sealing cuff 140 as well as a strip or band 142 of pleated fabric just above the sealing cuff. FIG. 9B is a laid flat plan view of a strip 144 of material and technique used to form the band 142 of pleated fabric. The strip 144 is generally rectangular and includes a series of tabs 146 spaced intermittently along an upper edge. The strip 144 is folded upon itself in a manner that places the tabs 146 adjacent one another, as shown. A needle 148 indicates the path of a suture or other filament used to sew the tabs 146 together to form the pleated skirt. If necessary, a seam (not shown) along the bottom edge may also be provided. Free ends of the strip 144 are then attached together to form the circular or conical band 142. The stacked folds of material of the strip 144 that form the pleats remain unconnected to each other so that blood can flow in between them, thus providing additional paravalvular leak protection. The band 142 of pleated fabric may be positioned directly above the plush sealing cuff 140 or anywhere up to the sealing ring 40.

Figure 10A:
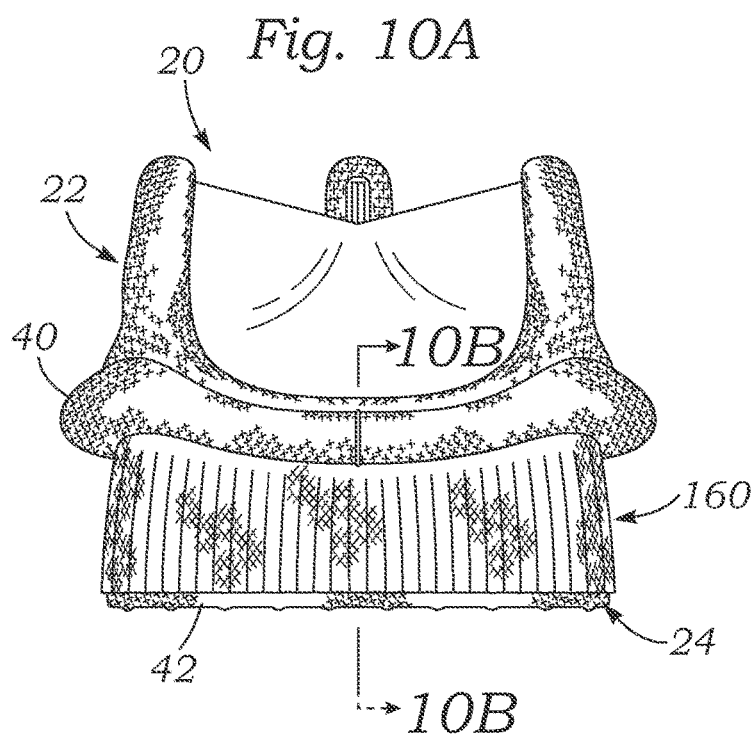
FIG. 10A is an elevational view of a hybrid heart valve where the anchoring stent has an elongated pleated fabric skirt placed over a flat fabric layer.
Figure 10B:
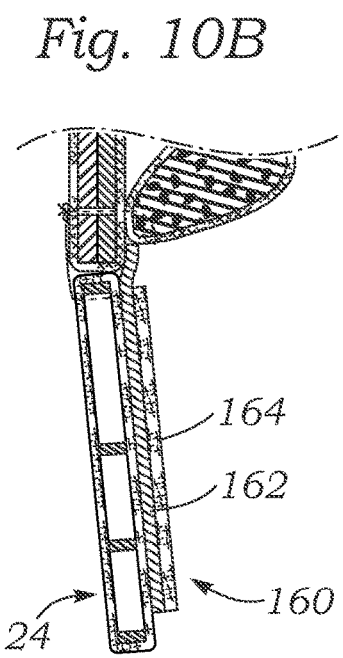
FIG. 10B is a vertical sectional view through a cusp portion of the heart valve.

In particular, FIG. 10A is an elevational view of a hybrid heart valve where the anchoring stent 24 has an elongated pleated skirt 160 of fabric placed over a flat fabric layer 42. The skirt 160 may be attached to the underlying fabric around the stent 24 or just an upper edge may be attached so that the pleated skirt 160 forms more of a curtain. The pleated skirt 160 desirably extends between a lower edge of the sealing ring 40 into close proximity with a lower end of the anchoring stent 24. The pleated skirt 160 may be formed in essentially the same manner as described above with respect to FIG. 9B, in that a strip of material is folded upon itself to form the pleats. FIG. 10B is a vertical sectional view through a cusp portion of the heart valve, and indicates the two-layer structure of the pleated skirt 160. Namely, the section line passes through an inner layer 162 of the strip of fabric that forms the skirt 160, while passing directly down through a slit between the separate pleats so as to show a pleat 164 folded on top of the inner layer 162. Once again, because the pleated skirt 160 extends downward directly below the sealing ring 40, it provides good leak prevention between the sealing ring and anchoring stent 24. The pleating helps keep the radial profile slim while filling spaces between the frame 24 and the surrounding anatomy.

Figure 11B:
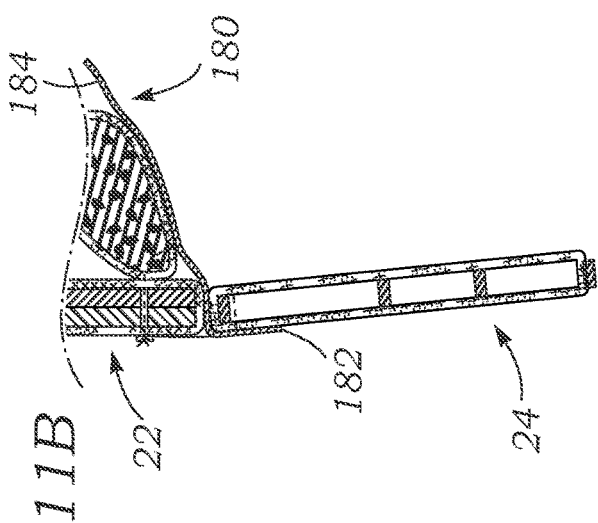
FIGS. 11B and 11C are vertical sectional and bottom plan views, respectively.
Figure 11A:
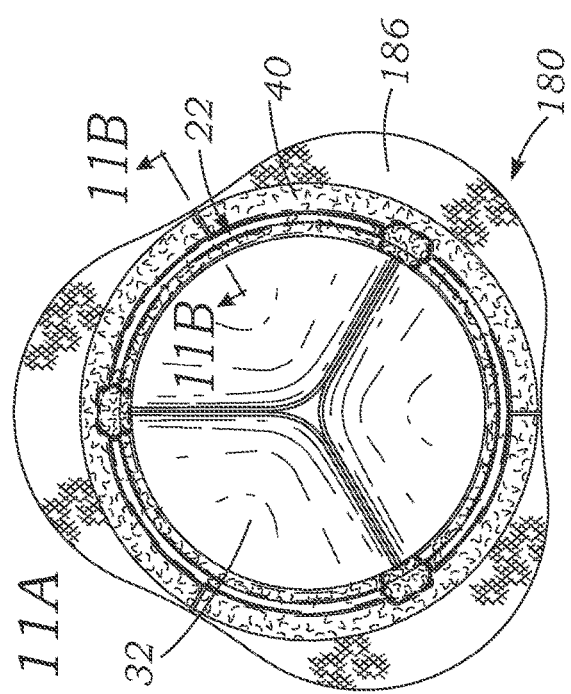
Figure 11D:
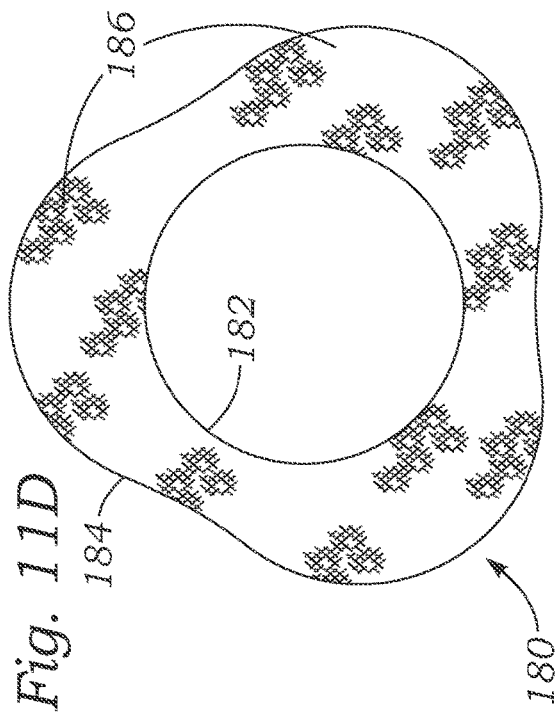
FIG. 11D is a flattened plan view of the fabric flap in isolation.

FIGS. 11A-11D illustrate a still further hybrid heart valve having a loose fabric flange or flap 180 positioned directly under a sealing ring 40 around a non-expandable valve member 22. FIG. 11D shows the flap 180 separated and laid-out in plan view in an annular shape. In a preferred embodiment, the flap 180 is a thin fabric such as polyethylene terephthalate (PET). The flap 180 includes a circular inner edge 182 and an undulating outer edge 184 which forms a series of outwardly-protruding lobes 186 around its circumference. Prosthetic heart valves typically include three leaflets 32 which are supported by the aforementioned internal stent structure of the valve member 22. In the embodiment illustrated in FIG. 1C, the internal support structure includes an undulating wireform 34 and an outer band-like stent 36 to which leaflet tabs 38 connect, all covered by fabric. The structure forms three commissure posts 28 which are shown in the top view of FIG. 11A.

Figure 11C:
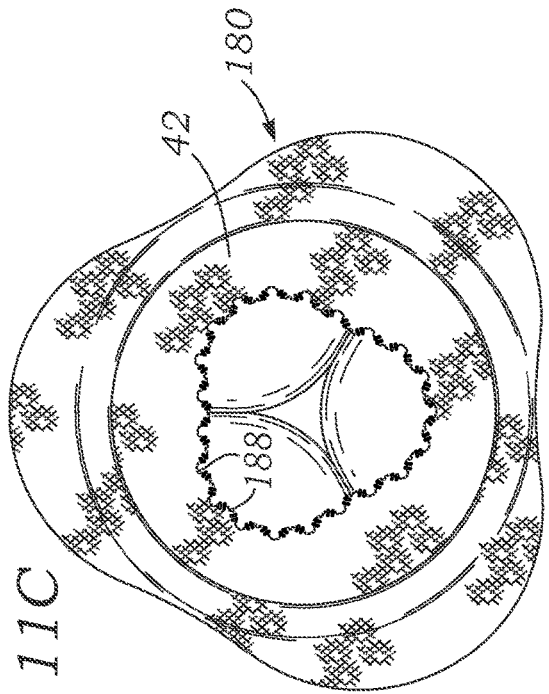

The sectional view of FIG. 11B indicates that the flap 180 extends under the sealing ring 40 and between the stent structure of the valve member 22 and the anchoring stent 24. The inner edge 182 may be secured to an inside wall of the stent 24, while the outer edge 184 remains free. The outer edge 182 may extend outward beyond the sealing ring 40 by about 10-20% of the diameter of the valve member 22. Alternatively, the outer edge 184 may be intermittently secured to the sealing ring 40 so as to form the pockets of sort, as discussed above. When assembled, the flap 180 forms three lobes 186 that are centered at each of the three commissure posts 28, as seen in FIG. 11A. Because of the anatomy of the aortic valve, the native commissures rise up adjacent to the prosthetic commissures 28. Although the sealing ring 40 is undulating, there may be some mismatch depending on the specific patient, and the outwardly-projected lobes 186 help seal this area. FIG. 11C also shows the outwardly-projecting lobes 186 from the bottom of the hybrid heart valve. The lower end of the expandable anchoring stent 24 may be crimped into a rounded triangular configuration with the fabric 42 being secured thereto with stitches 188.

Plush Fabric

FIG. 12A is an elevational view of a hybrid heart valve including a plush fabric layer 200 secured over a fabric-covered anchoring stent 24. An upper edge 202 of the plush fabric layer 200 has a scalloped or undulating shape which rises up at the commissures 28 of the valve member 22 to cover the entire anchoring stent 24 at those locations and dips down at the cusps 30. FIG. 12B is a vertical sectional view through a cusp portion of the heart valve showing a folded over configuration for the plush fabric layer 200. As mentioned above, because the anatomical area around the prosthetic valve commissures 28 is uneven, the provision of the plush fabric 200 up closely against the sealing ring 40 at the commissures helps prevent leaks in this area.

FIG. 13A is a still further hybrid heart valve where two plush fabric layers of different size are attached over a fabric-covered anchoring stent. Namely, a first or inner layer 210 of plush fabric is secured over the entire anchoring stent 24 which is already covered with a thin fabric 42. Over the top of this is a second or outer layer 212 of plush fabric which is desirably provided in a narrow band located at the inflow or lower end of the anchoring stent. As seen in the vertical sectional view of FIG. 13B, these layers 210, 212 are single layers, e.g., not folded upon each other, but may also be doubled up. The narrow band that forms the outer layer 212 may be relocated to just below the sealing ring 40 of the valve member 22, but positioning it at the lower end of the stent 24 leaves room underneath the sealing ring 40 for seating around the native annulus.

Figure 14A:
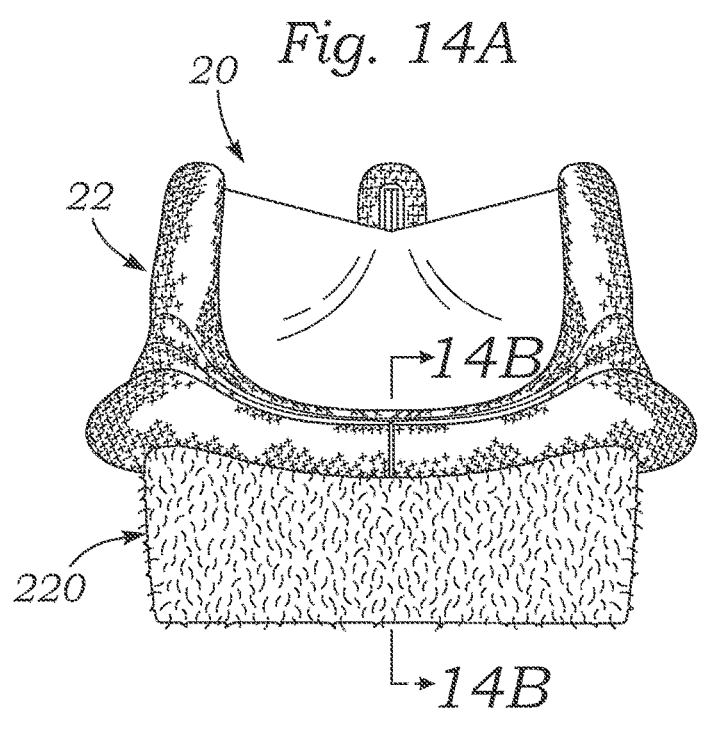
FIG. 14A is an elevational view of a hybrid heart valve where a tapered plush fabric layer is attached over a fabric-covered anchoring stent.
Figure 14B:
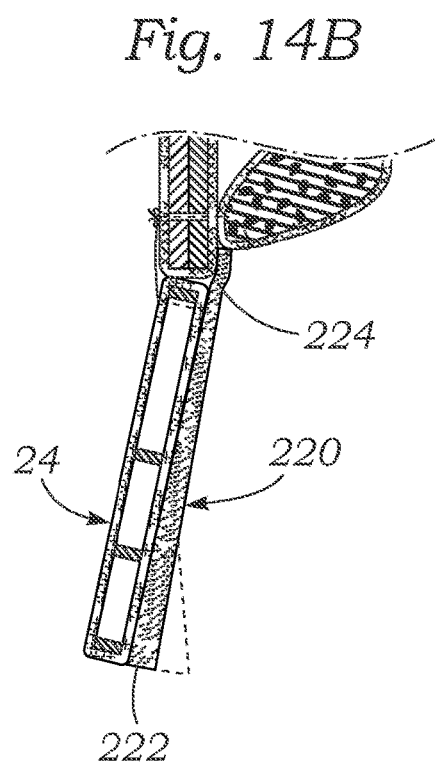
FIG. 14B is a vertical sectional view through a cusp portion of the heart valve.

FIG. 14A illustrates another hybrid heart valve where a tapered plush fabric layer 220 is attached over a fabric-covered anchoring stent 24. As seen in FIG. 14B, the fabric layer 220 has a radially wider lower end 222 than an upper end 224. The tapered fabric layer 220 desirably covers the entire exterior of the anchoring stent 24, but may also be provided in a shorter band as desired. The taper of the fabric layer 220 may be linear, as shown, or nonlinear so as to have a flared lower end 222 (shown in phantom). Varying the thickness of the fabric layer 220 in this regard is facilitated by crimping the anchoring stent 24 radially inward more at its lower end, such that the additional fabric does not stick out and interfere with delivery of the valve.

Figure 15A:
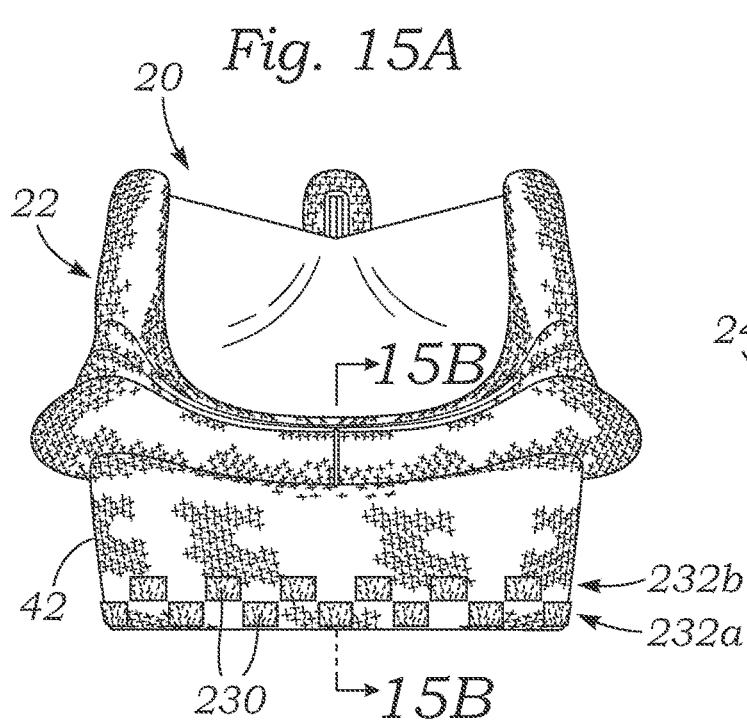
FIG. 15A is an elevational view of a hybrid heart valve where a plurality of patches of plush fabric are attached around a lower end of a fabric-covered anchoring stent in an alternating checkered pattern.
Figure 15B:
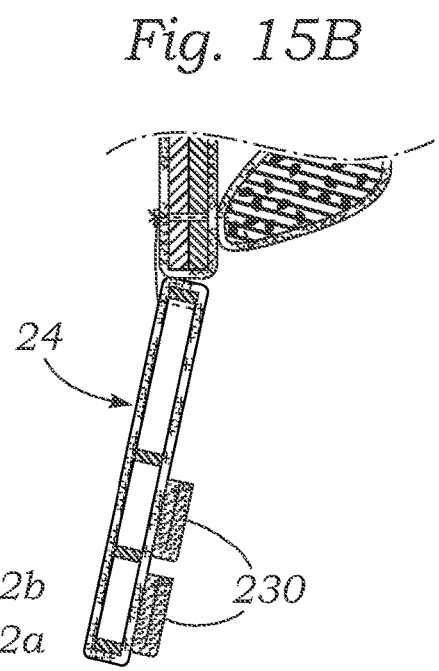
FIG. 15B is a vertical sectional view through a cusp portion of the heart valve.

FIG. 15A shows a hybrid valve with a fabric-covered anchoring stent 24 having a plurality of patches 230 of plush fabric attached around a lower end in an alternating pattern. That is, the patches 230 are provided in two horizontal rows; a first row 232a located along the lower end of the stent 24 and a second row 232b directly above the first row. Each row 232a, 232b has a series of evenly spaced rectangular patches 230. The patches in the two rows 232a, 232b are vertically offset so as to form a checkered pattern of sorts. Alternating the patches 230 in this regard helps limit the overall radial profile of the fabric-covered stent 24. FIG. 15B is a vertical sectional view through a cusp portion of the heart valve showing that each of the patches 230 is formed by a folded over piece of plush fabric secured to the thin fabric 42 of the stent 24.

Expanded Sealing Ring

FIG. 16A is an elevational view of a hybrid heart valve having a lower plush fabric cuff 240 surrounding a fabric-covered anchoring stent. In addition, the valve features and an irregular sealing ring 242 around a non-expandable valve member. The sealing ring 242 has an undulating shape with upwardly curved commissure regions 244 alternating with downwardly curved cusp regions 246. A lower edge 248 of the sealing ring 242 extends considerably further downward toward the plush cuff 240 in the cusp regions 246 than with a conventional sealing ring. This is also seen in the vertical sectional view of FIG. 16B. In a preferred embodiment, the vertical dimension of the sealing ring 242 increases from a first value at the commissure regions 244 to approximately 1.5 or two times as large at the cusp regions 246. Another way to state this is that the lower edge 248 dips down in the cusp regions 246 into proximity with the lower plush cuff 240. Another way to define this is that the sealing ring 242 at the cusp regions 246 extends down approximately 50% of the vertical height of the anchoring stent 24.

FIG. 17A shows another hybrid heart valve where again a lower plush fabric cuff 260 is provided over a fabric-covered anchoring stent 24, and an irregular sealing ring 262 extends around a non-expandable valve member. In this embodiment, the sealing ring 262 comprises commissure bulges 264 below the valve commissures 28 alternating with conventional thickness cusp regions 266. That is, a lower edge 268 of the sealing ring 262 dips down considerably farther at the commissure regions 264 that at the cusp regions 266. In one embodiment, the lower edge 268 extends down about 50% of the vertical height of the anchoring stent 24 into proximity with the lower plush cuff 260.

FIGS. 17B and 17C are vertical sectional view through a commissure portion of the heart valve adjacent a surrounding target annulus during implant. The enlarged commissure bulges 264 are shown in contact with the surrounding anatomy. When the anchoring stent 24 is expanded, the bulges 264 at the commissure regions help prevent paravalvular leakage between the sealing ring 262 and the anchoring stent 24 by conforming to irregular anatomical surfaces and filling spaces. Optionally, an implantation suture 270 may be utilized at the commissure regions to help compress and conform the commissure bulges 264 against the surrounding anatomy. In this configuration, only three implantation sutures 270 are used, one at each of the commissures, to help speed up the valve replacement surgery.

O-Rings

Figure 18A:
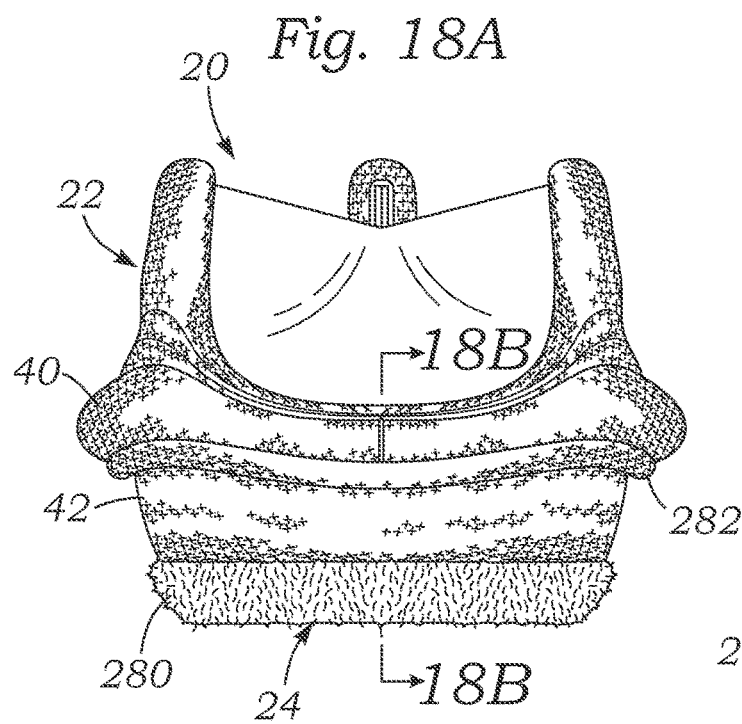
FIG. 18A is an elevational view of a hybrid heart valve having a lower plush fabric cuff over a fabric-covered anchoring stent as well as a fabric-covered elastomeric O-ring around the stent positioned just below a sealing ring of a non-expandable valve member.
Figure 18B:
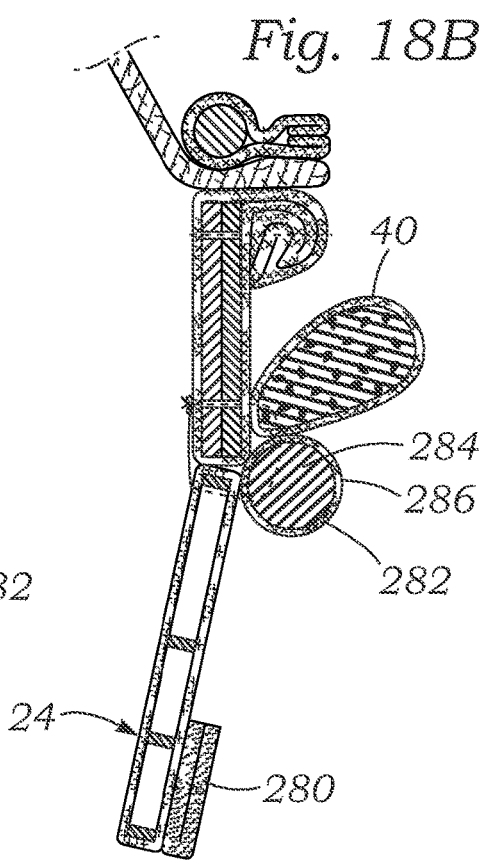
FIG. 18B is a vertical sectional view through a cusp portion of the heart valve.

FIG. 18A illustrates a hybrid heart valve 20 with a lower plush fabric cuff 280 over a fabric-covered anchoring stent 24. A fabric-covered elastomeric O-ring 282 extends around the stent 24 just below a regular sealing ring 40 circumscribing a non-expandable valve member 22. FIG. 18B is a vertical sectional view through a cusp portion of the heart valve showing the location of the O-ring 282 in the corner or junction formed between the sealing ring 40 and the anchoring stent 24. The O-ring 282 may comprise an inner core 284 of a compressible material such as silicone with a fabric cover 286.

Figure 19A:
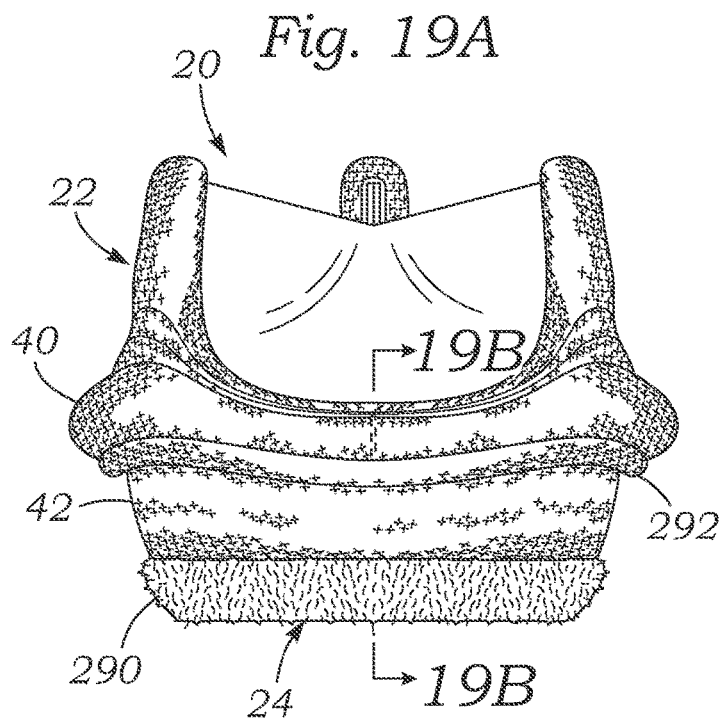
FIG. 19A is an elevational view of a hybrid heart valve having a lower plush fabric cuff over a fabric-covered anchoring stent as well as a fabric O-ring around the stent positioned just below a sealing ring of a non-expandable valve member.
Figure 19B:
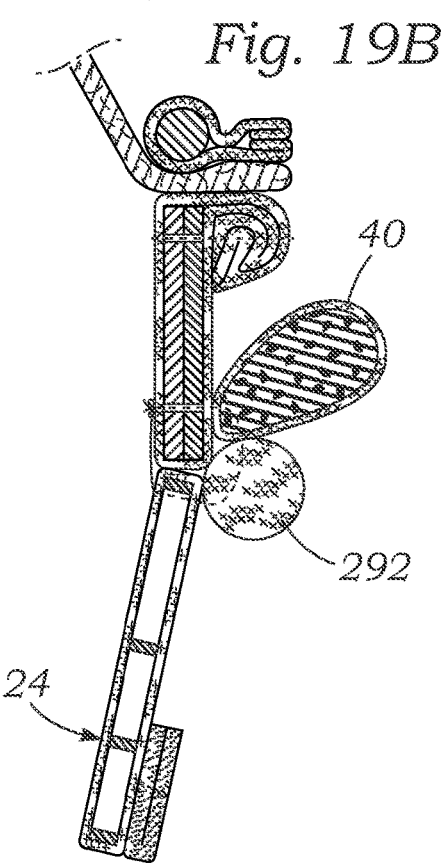
FIG. 19B is a vertical sectional view through a cusp portion of the heart valve.

FIG. 19A shows another hybrid heart valve 20 with a lower plush fabric cuff 290 over a fabric-covered anchoring stent and a fabric O-ring 292 around the stent positioned just below the sealing ring. As seen in FIG. 19B, the O-ring 292 again is attached in a corner or junction between the sealing ring 40 and the anchoring stent 24 and in this embodiment comprises only fabric. The plush fabric cuff 290 may be in the form of a cylindrical O-ring, as shown, or simply a narrow band or folded tube of the plush fabric secured directly under the sealing ring 40.

Inclusion of the O-rings 282, 292 underneath the sealing ring 40 in the valves seen in FIGS. 18-19 provides additional paravalvular sealing between the sealing ring and the anchoring stent 24. This functions much like the irregular sealing rings 242, 262 in FIGS. 16-17 in that more compressible material is provided between the dimensionally-stable valve member 22 and the expandable anchoring stent 24. Additional implantation sutures may be utilized through the O-rings 282, 292 which can be pulled taut to help further seal against the surrounding anatomy.

Figure 20A:
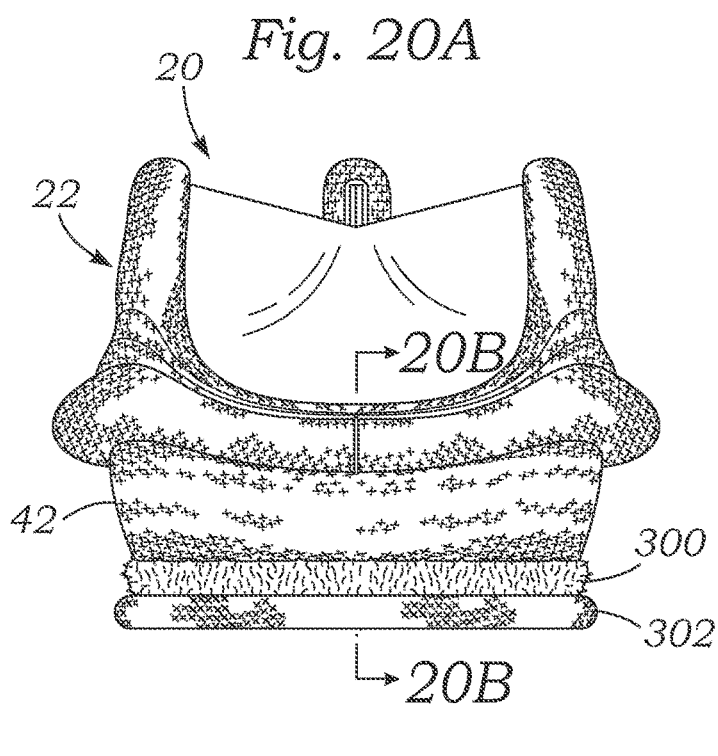
FIG. 20A is an elevational view of a hybrid heart valve having a lower plush fabric cuff over a fabric-covered anchoring stent as well as a fabric-covered elastomeric O-ring around a lower end of the cuff.
Figure 20B:
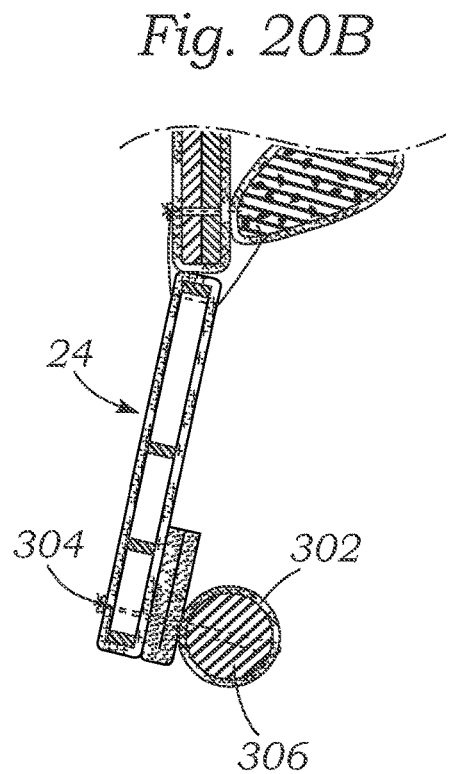
FIG. 20B is a vertical sectional view through a cusp portion of the heart valve.

FIG. 20A is a still further hybrid heart valve 20 again with a lower plush fabric cuff 300 over a fabric-covered anchoring stent 24. In addition, a fabric-covered elastomeric O-ring 302 surrounds and is attached to the cuff 300. FIG. 20B is a vertical sectional view through a cusp portion of the heart valve which shows an attachment suture 304 in a line of such sutures holding the O-ring 302 against cuff 300. In the illustrated embodiment, the O-ring 302 has an inner core 306 of compressible material such as silicone and a fabric covering, though the O-ring may also be entirely made of fabric. When the anchoring stent 24 expands outward into contact with the surrounding anatomy, the combination of the plush cuff 300 and surrounding O-ring 302 provide exemplary paravalvular sealing around the lower end of the stent. Moreover, the O-ring 302 on top of the cuff 300 helps to better secure the anchoring stent 24 against the surrounding tissue.

Miscellaneous Sealing Structures

Figure 21A:
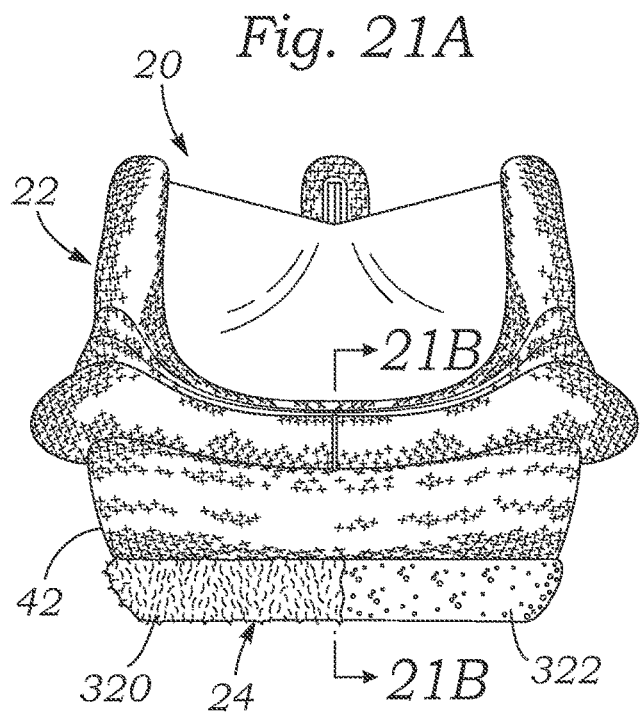
FIG. 21A is an elevational view of a hybrid heart valve having a lower plush fabric cuff over a foam strip attached around a lower end of a fabric-covered anchoring stent.
Figure 21B:
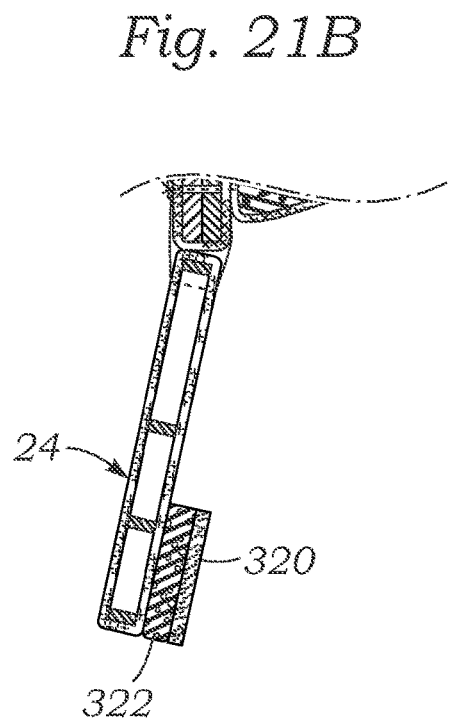
FIG. 21B is a vertical sectional view through a cusp portion of the heart valve.

In FIG. 21A, a hybrid heart valve features a lower plush fabric cuff 320 secured around a foam strip 322 that is attached around a lower end of a fabric-covered anchoring stent 24. With reference to FIG. 21B, the fabric cuff 320 and foam strip 322 are shown attached coincident with the lower end of the anchoring stent 24 and directly on top of one another. The foam strip 322 may be made of a memory foam (i.e., viscoelastic foam) which conforms better to uneven or heavily-calcified region surrounding the valve and has somewhat less elasticity so as to rebound less. Memory foam consists mainly of polyurethane as well as additional chemicals increasing its viscosity and density. It may be referred to as "viscoelastic" polyurethane foam, or low-resilience polyurethane foam (LRPu). The foam bubbles or 'cells' are open, effectively creating a matrix through which air can move. The cuff 320 and strip 322 may be secured with sutures, adhesives, or other such attachment means. Again, the combination of the compressible foam strip 322 with the plush fabric cuff 320 over the top provides good sealing around the lower end of the stent.

FIG. 22A is another hybrid heart valve 20 with a fabric-covered anchoring stent 24 around which is provided a hydrophilic swellable band 340. The band 340 preferably has an inner core 342 of swellable material and a fabric cover 344. FIG. 22B is a partial cutaway and sectional view showing the band 340 after swelling. In a preferred embodiment, the band 340 extends along the entire height of the anchoring stent 24, or at least a majority of the height. The material of the inner core 342 is hydrophilic such as a hydrogel designed to swell upon absorption of water after implant. Thus, the anchoring stent 24 is first expanded into contact with the surrounding anatomy, after which the inner core 342 starts to swell as indicated by the outward arrows and fills in any uneven spaces between the stent and anatomy. The band 340 thus remains thin during implantation and only swells over time after implant.

With reference to FIG. 23A, a hybrid heart valve 20 features a fabric-covered anchoring stent 24 around the lower end of which is provided a fabric-covered foam band 350. The band 350 preferably has an inner core 352 of foam material and a surrounding fabric cover 354, as seen in FIG. 23B. Attachment sutures 356 are shown connecting the band 350 to the outside of the stent 24, though the band may also be attached using adhesives or the like. The material of the inner core 352 may be open- or closed-cell foam, and may be memory foam as described above. Indeed, any of the sealing structures having inner compressible cores disclosed herein may be formed of a variety of materials, in particular memory foam.

Alternatively, the band 350 shown in FIG. 23A represents a coating over a plush fabric cuff on the anchoring stent 24. Providing such a coating 350 smooth out the otherwise fuzzy fabric cuff which facilitates advancement through the body and implantation at the annulus. The coating 350 be bioresorbable so as to dissolve once in contact with the tissue either by moisture or by heat, or other mechanisms. The coating 350 thus makes the seating procedure easier and may be seeded with chemicals that promote cell growth thereafter.

Figure 24A:
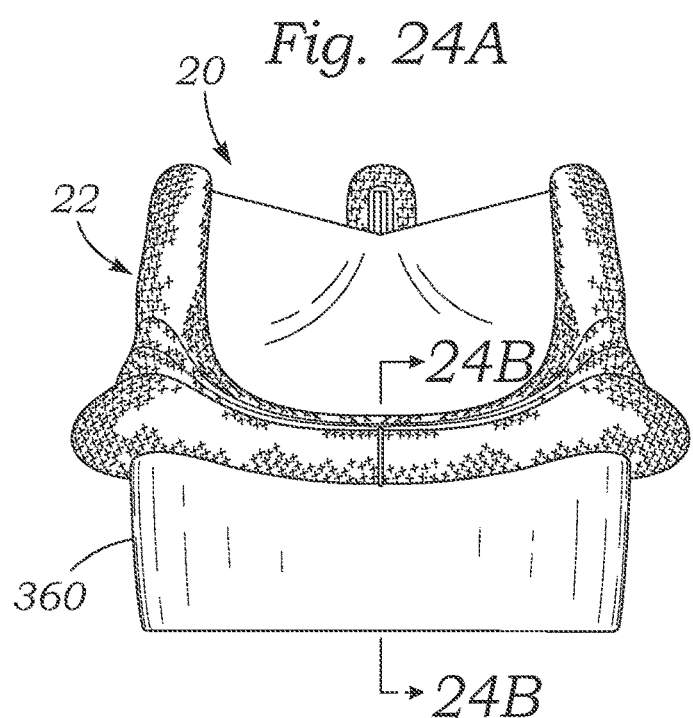
FIG. 24A is an elevational view of a hybrid heart valve where the fabric-covered anchoring stent has an external layer of tissue or adhesive material.
Figure 24B:
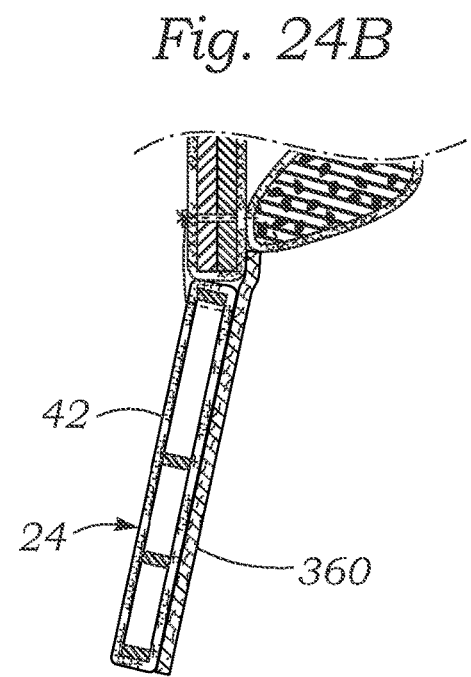
FIG. 24B is a vertical sectional view through a cusp portion of the heart valve.

FIG. 24A is an elevational view of a hybrid heart valve 20 where the fabric-covered anchoring stent 24 has an external layer 360 of bioprosthetic tissue or tissue adhesive material (e.g., fibrin glue) covering its entire external surface. The bioprosthetic tissue may be bovine pericardial sheet which accelerates tissue ingrowth after implant. FIG. 24B shows the layer 360 directly connected on the outside of the stent 24, which can be via sutures through the thin fabric cover 42, adhesives, or the like.

Alternatively, the external layer 360 may represent a foam that has been impregnated into the thin fabric 42 of the anchoring stent 24. The foam 360 may be activated upon illumination with UV light so that it expands and spreads outward toward the annulus, thus enhancing sealing and anchoring. The UV light eventually solidifies the foam 360.

Figure 25A:
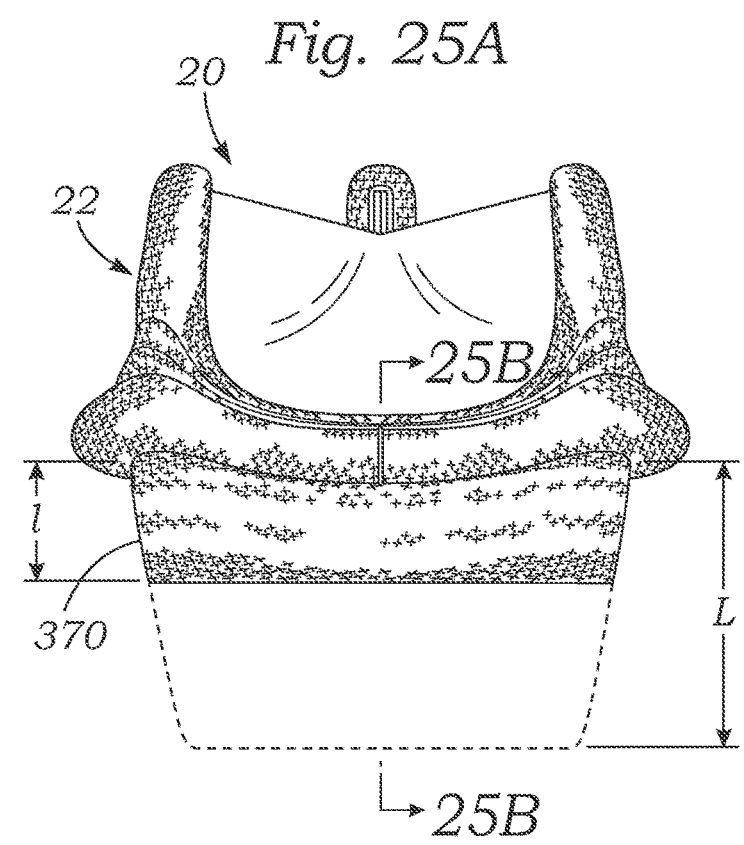
FIG. 25A is an elevational view of a hybrid heart valve having an extensible fabric positioned on the outside of a fabric-covered anchoring stent.
Figure 25B:
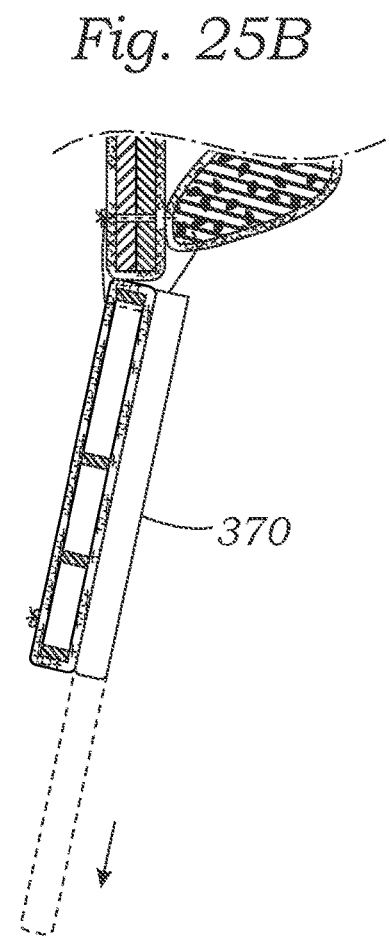
FIG. 25B is a vertical sectional view through a cusp portion of the heart valve indicating a direction that the fabric extends.

FIG. 25A illustrates another hybrid heart valve 20 where having an extensible fabric skirt 370 positioned on the outside of a fabric-covered anchoring stent 24. FIG. 25B is a vertical sectional view through a cusp portion of the heart valve indicating a direction that the fabric skirt 370 extends. Prior to implantation, extensible skirt 370 has a length e of approximately the vertical dimension of the anchoring stent 24. During or after implant, the skirt 370 may be pulled downward as indicated in FIG. 25B so as to provide material below the valve for sealing against paravalvular leakage. For example, the skirt 370 may initially be provided in a bunched-up state so that it may be stretched longer. The final length L may be up to about double the initial length e.

Interactive Sealing Structures

As mentioned above, the present application may involve combination of various sealing solutions disclosed herein, as long as they are not mutually exclusive. The following discussion pertains to interactive sealing devices which are deployed during implantation of the hybrid heart valve. Any of these interactive solutions may be utilized with any of the fixed sealing structures disclosed above.

In a first example, FIGS. 26A and 26B disclose a hybrid heart valve 20 mounted on a distal end of a delivery system 50 having an elongated malleable handle shaft, as seen above in FIGS. 4A and 4B. The shaft terminates in a generally tubular adapter 54 that couples to a valve holder 56 secured to the valve 20 with sutures, for example, between lower ends of three legs 58 of the valve holder 56 and the sealing ring 40 of the valve.

As mentioned, the heart valve 20 may be similar to that of the prior art, or any of the various heart valves disclosed herein. The heart valve 20 is shown exploded from a coiled layer 380 of fabric in FIG. 26A which is assembled over the fabric-covered anchoring stent 24 in FIG. 26B. The layer 380 is desirably formed of a stretchy fabric which may be pulled taut around the stent 24 so that its free ends 382 overlap. FIG. 26B shows the assembled valve with the layer 380 held in its stretched configuration by sutures, clips or the like. In a preferred embodiment, a suture attached to the holder 56 maintains the layer 380 in its stretched configuration and can be severed and removed to release the layer 380. The layer 380 is initially stretched tight around the anchoring stent 24 to minimize its radial profile for ease of delivery of the valve.

Once the valve is seated, tension on the layer 380 may be released. FIG. 26C shows the assembled valve after tension in the stretched fabric layer 380 has been released to create bunches in the layer. The release of tension can be accomplished by cutting the suture(s) that hold the layer 380 in tension, or by otherwise removing clips or other such structure. When the tension is released, the layer 380 uncoils and tends to form bunches as indicated by the wavy lines which help seal around the anchoring stent 24.

FIGS. 27A-27C show another hybrid heart valve 20 having a fabric-covered anchoring stent 24 and an inflatable sealing ring 390 around a non-expandable valve member 22. The sealing ring 390 may have a chamber 392 therein and a fill valve 394 located on an upper surface thereof so as to be accessible from the outflow side of the valve 20 via a fill tube 396. FIGS. 27B and 27C are vertical sectional views through a cusp portion of the heart valve showing inflation of the sealing ring 390 with a hydrogel 398, for example. While being inflated, the hydrogel 398 expands the sealing ring 390 against the surrounding anatomy to fill any spaces therebetween. The material of the sealing ring 390 is desirably stretchable to enable uneven expansion from inflation into spaces formed by the surrounding uneven anatomy. Eventually, the hydrogel 398 cures to prevent fluid flow through the sealing ring 390, and of course the fill tube 396 is removed.

Next, FIGS. 28A-28C are vertical sectional views through a hybrid heart valve illustrating a procedure for introducing a curable sealing adhesive or medium 400 between a fabric-covered anchoring stent 24 and surrounding tissue. The median may be glycerin or a gelatin-based tissue glue/sealant that can be cured by light. In FIG. 28A the valve has been advanced so that the sealing ring 40 is above the native annulus 402 while the anchoring stent 24 is located below in the adjacent chamber of the heart (the left ventricle in the case of the aortic annulus). One or more fill tubes 404, which may be preinstalled around the valve, extend between the sealing ring 40 and the annulus 402, terminating in the region between the constricted (un-deployed) anchoring stent 24 and the adjacent chamber. The curable sealing medium 400 in liquid form is then injected between the stent and the chamber wall. Again, there may be a single fill tube 404, or an array of them completely surrounding the valve.

FIG. 28B shows outward radial expansion of the anchoring stent 24 against the surrounding chamber. The liquid sealing medium 400 is compressed into a relatively consistent layer. Finally, FIG. 28C shows introduction of an instrument 406 having a plurality of curing lights 408 mounted thereon through the valve and inside of the anchoring stent 24. Illumination of the lights 408 causes relatively quick curing (solidification) of the sealing medium 400. The instrument 406 may be introduced through the valve orifice and then rotated around the inside of the anchoring stent for, or there may be multiple such instruments in a circumferential array. The light-cure tissue sealing adhesive or medium 400 can be cured by UV light such as by lights with specific wavelength (e.g., 360-375 nm or 440-480 nm). The lights 408 on the instrument 406 can also be integrated into the tip of the delivery system 50.

FIGS. 29A-29C illustrate a procedure for implanting a hybrid heart valve using a self-adhesive precursor band 420 pre-installed just below the annulus. The precursor band 420 desirably has a size which closely matches the size of the chamber below the native annulus. In the illustrated embodiment, the left ventricle LV is located just below the aortic annulus AA. Consequently, the band 420 may be sized so as to closely fit within the left ventricle LV just below the aortic annulus AA, or may be somewhat adjustable to compensate for mismatches in size. The band 420 includes a series of self-adhesive outer patches 422 that enable it to be secured to the left ventricle LV, as seen in FIG. 29B.

FIG. 29B shows a hybrid heart valve 20 having the anchoring stent 24 thereon being lowered into position at the aortic annulus AA. Again, the heart valve 20 may be similar to those of the prior art, or any of the embodiments disclosed herein. The heart valve 20 has a fabric-covered anchoring stent 24, and the precursor band 420 features a series of patches 424 having miniature hooks thereon.

FIG. 29C shows expansion of the anchoring stent 24 contact with the precursor band 420. Because of the miniature hooks on the patches 424, the anchoring stent 24 is better secured below the annulus. That is, the hooks on the patches 424 connect to the fabric on the stent 24 as with any hook and loop (e.g., Velcro® fastener, Velcro BVBA) fastening system.

While certain embodiments have been described, it is to be understood that the words which have been used are words of description and not of limitation. Therefore, changes may be made within the appended claims without departing from the true scope of the disclosure.

What is claimed is:

1. A hybrid prosthetic heart valve for implant at a heart valve annulus, comprising:
 a valve member having a non-expandable, non-collapsible annular support structure defining a flow orifice and having an inflow end, the valve member having valve leaflets attached to the support structure and mounted to alternately open and close across the flow orifice and a compressible sealing ring encircling the inflow end of the annular support structure;
 an expandable stent secured to the inflow end of the annular support structure and extending therefrom to an inflow edge, the stent comprising a generally tubular stent frame formed by struts, the stent frame being covered by a thin fabric layer; and a flap of fabric having a circular inner edge secured between the stent and the valve member and an outer edge that extends outward adjacent and to an inflow side of the sealing ring and radially outward beyond the sealing ring.

2. The heart valve of claim 1, wherein the flap of fabric has an undulating outer edge which forms a series of outwardly-protruding lobes around its circumference.

3. The heart valve of claim 2, wherein the annular support structure of the valve member includes three evenly-spaced commissure posts alternating with three arcuate cusps, and there are three outwardly-protruding lobes each centered about one of the commissure posts.

4. The heart valve of claim 3, wherein the outwardly-protruding lobes each extend outward beyond the sealing ring by between about 10-20% of the diameter of the valve member.

5. The heart valve of claim 2, wherein the outer edge extends outward beyond the sealing ring by between about 10-20% of the diameter of the valve member.

6. The heart valve of claim 1, wherein the outer edge extends outward beyond the sealing ring by between about 10-20% of the diameter of the valve member.

7. The heart valve of claim 1, wherein the inner edge of the flap of fabric extends downward within the stent and is secured thereto with sutures.

8. The heart valve of claim 1, wherein the outer edge is intermittently secured to the sealing ring with sutures so as to form pockets between the sutures.

9. The heart valve of claim 1, wherein the flap of fabric is made of polyethylene terephthalate.

10. The heart valve of claim 9, wherein the annular support structure of the valve member includes three evenly-spaced commissure posts alternating with three arcuate cusps, and the flap of fabric has an undulating outer edge which forms a series of outwardly-protruding lobes around its circumference each centered about one of the commissure posts.

11. The heart valve of claim 10, wherein the inner edge of the flap of fabric extends downward within the stent and is secured thereto with sutures while the outer edge remains free.

* * * * *